(12) United States Patent
Alt et al.

(10) Patent No.: US 10,137,143 B1
(45) Date of Patent: Nov. 27, 2018

(54) PREVENTING TUMOR DEVELOPMENT AND METASTASIS

(71) Applicant: The Administrators of the Tulane Educational Fund, New Orleans, LA (US)

(72) Inventors: Eckhard Alt, New Orleans, LA (US); Reza Izadpanah, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 14/814,130

(22) Filed: Jul. 30, 2015

Related U.S. Application Data

(60) Provisional application No. 62/031,021, filed on Jul. 30, 2014.

(51) Int. Cl.
*A61K 31/7105* (2006.01)
*A61K 41/00* (2006.01)
*A61K 47/48* (2006.01)
*A61K 31/713* (2006.01)

(52) U.S. Cl.
CPC ........ *A61K 31/7105* (2013.01); *A61K 31/713* (2013.01); *A61K 41/00* (2013.01); *A61K 47/484* (2013.01); *A61K 47/48569* (2013.01); *A61K 47/48623* (2013.01)

(58) Field of Classification Search
None
See application file for complete search history.

(56) References Cited

U.S. PATENT DOCUMENTS

| 6,004,814 A * | 12/1999 | Bennett ............. | C12N 15/1138 435/375 |
| 2008/0234941 A1* | 9/2008 | Jackson ................ | C12N 15/111 702/19 |
| 2009/0221674 A1* | 9/2009 | Sahin ................. | C07K 14/4748 514/44 A |

FOREIGN PATENT DOCUMENTS

WO    WO2014030602    2/2014

OTHER PUBLICATIONS

Liu et al. (2012 Inhibition of Glioma Cell Lysosome Exocytosis Inhibits Glioma Invasion. PLoS ONE 7(9): e45910).*
Hunter, C. A. (2007). "Act1-ivating IL-17 inflammation." Nat Immunol 8(3): 232-4.
Qian, Y., C. Liu, et al. (2007). "The adaptor Act1 is required for interleukin 17-dependent signaling associated with autoimmune and inflammatory disease." Nat Immunol 8(3): 247-56.
Senst, C., T. Nazari-Shafti, et al. (2013). "Prospective dual role of mesenchymal stem cells in breast tumor microenvironment." Breast Cancer Res Treat 137(1): 69-79.
Xia YF, et al., Identification of alternatively spliced Act1 and implications for its roles in oncogenesis, Biochem. Biophys. Res. Commun. 296 (2): 406-12 (2002).

* cited by examiner

*Primary Examiner* — Kimberly Chong
(74) *Attorney, Agent, or Firm* — Boulware & Valoir

(57) ABSTRACT

Treatment of tumors, especially breast cancer or glioblastoma tumors, by silencing RAB27A and/or TRAF3IP2, compositions and methods for same.

13 Claims, 12 Drawing Sheets

Specification includes a Sequence Listing.

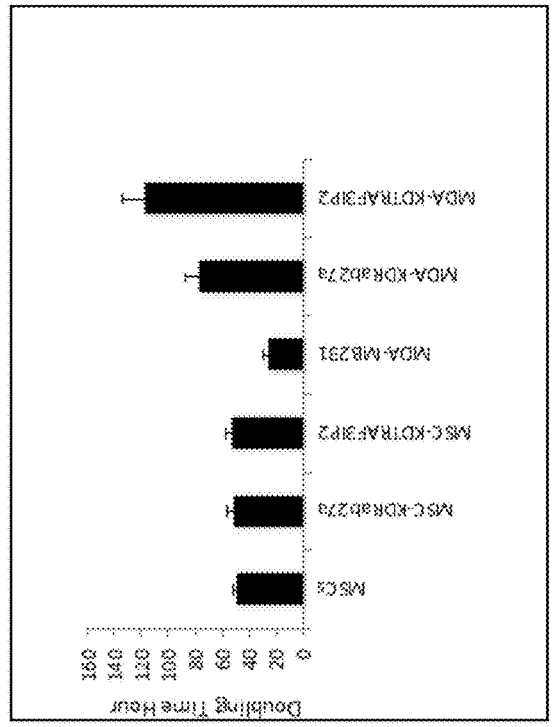
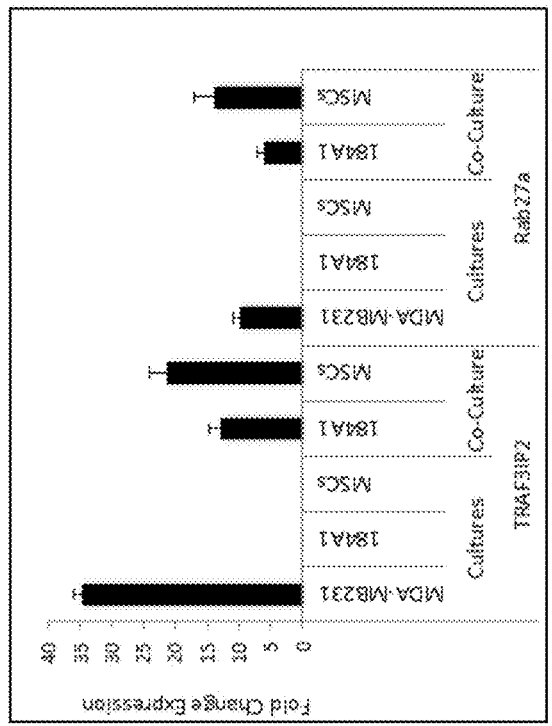
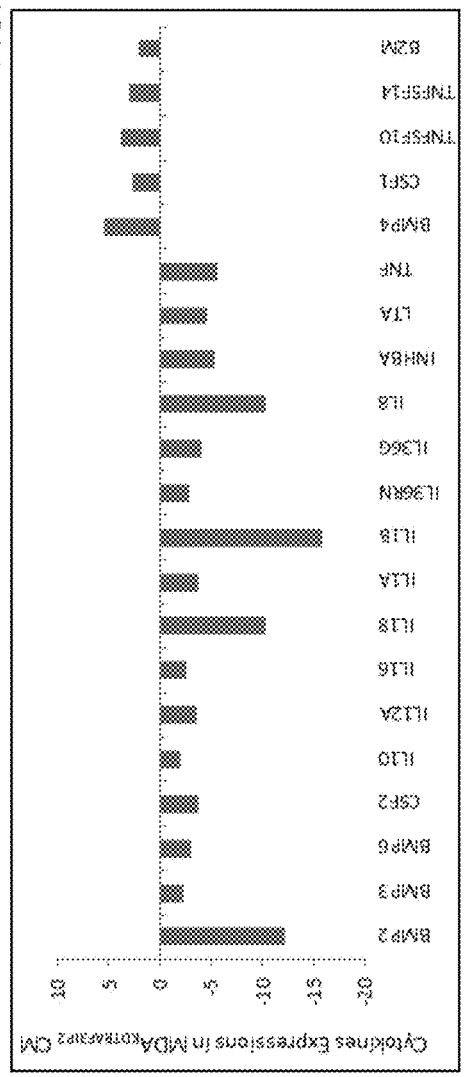
FIG. 4A
FIG. 4B
FIG. 4C

Figure 6
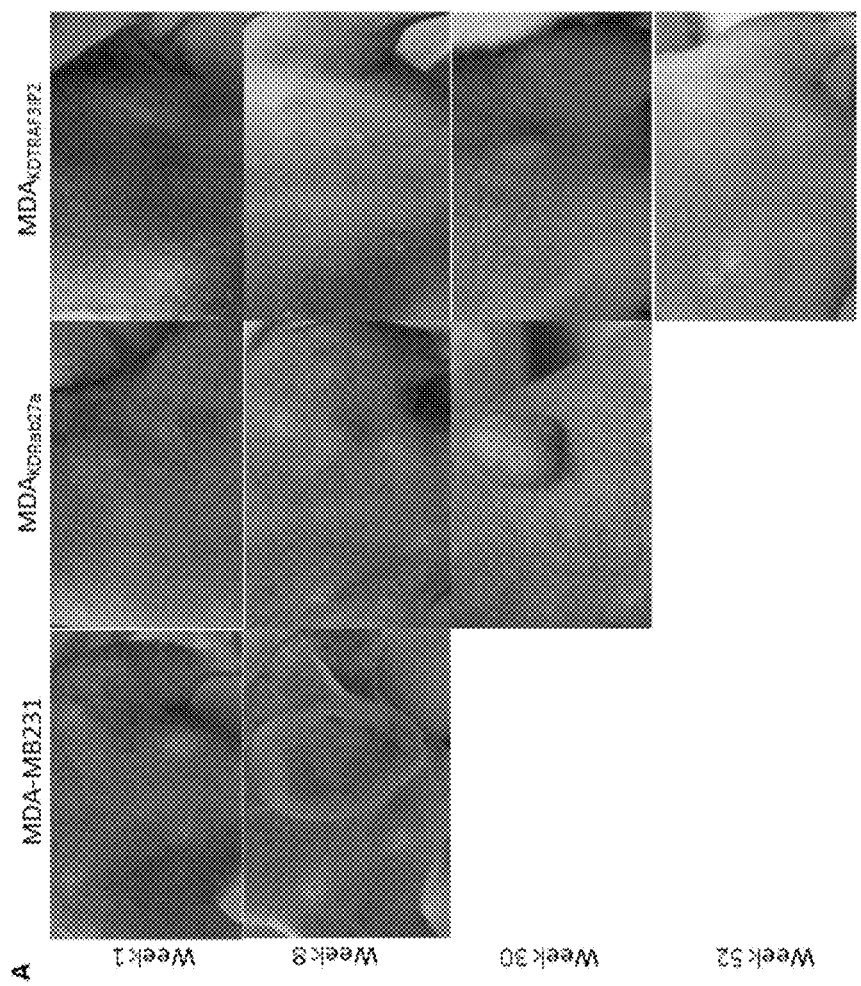
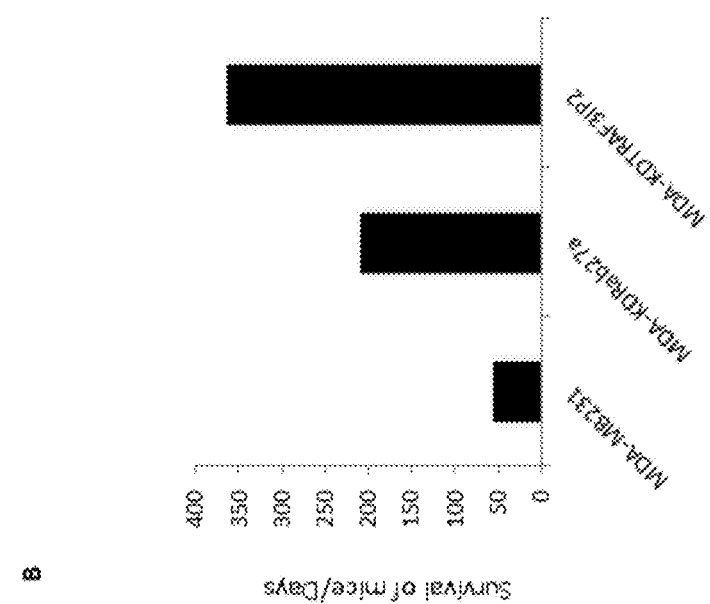

FIGURE 8

| Name | Sequence |
|---|---|
| RAB27A, variant 1 | NM_004580.4 (3,474 nt) |
| RAB27A, variant 2 | NM_183234.2 (3,455 nt) |
| RAB27A, variant 3 | NM_183235.2 (3,464 nt) |
| RAB27A, variant 4 | NM_183236.2 (3,415 nt) |
| RAB27A, variant X1 | XM_011521852.1 (3,663 nt) |
| RAB27A, variant X2 | XM_011521853.1 (3,744 nt) |
| RAB27A, variant X3 | XM_011521854.1 (3,536 nt) |
| RAB27A, variant X4 | XM_011521855.1 (3,528 nt) |
| RAB27A, variant X5 | XM_011521856.1 (3,314 nt) |
| RAB27A, variant X6 | XM_005254576.3 (3,342 nt) |
| TRAF3IP2 antisense RNA 1, variant 1 | NR_034108.1 (4,943 nt) |
| TRAF3IP2 antisense RNA 1, variant 2 | NR_034109.1 (4,652 nt) |
| TRAF3IP2 antisense RNA 1, variant 3 | NR_034110.1 (2,195 nt) |
| TRAF3IP2 | NM_011164281.2 (6,241 nt) (SEQ ID NO. 7) |
| TRAF3IP2, variant 2 | NM_147686.3 (6,244 nt) |
| HUMAN TRAF3IP2 SILENCER Variant 1: TRCN0000158477 | SEQ ID NO. 1: CCGGGCATGGAACTATCATTACCATTCTCGAGAATGGTAATGATAGTTCCATGTTTTT |
| HUMAN TRAF3IP2 SILENCER Variant 2: TRCN0000005297 | SEQ ID NO. 2 CCGGGCCGTGATGATAATCGTAGCAACTCGAGTTGCTACGATTATCATCACGGTTTTTG |
| HUMAN TRAF3IP2 SILENCER Variant 3: TRCN0000160964 | SEQ ID NO. 3 CCGGGCTTCAGAACACTCATGTCTACTCGAGTAGACATGAGTGTTCTGAAGCTTTTTG |
| HUMAN RAB27A SILENCER Variant 1: TRCN0000005296 | SEQ ID NO 4: CCGGGGGATCAGTTAAGTGAAGAAACTCGAGTTTCTTCACTTAACTGATCCGTTTTT |
| HUMAN RAB27A SILENCER Variant 2: TRCN0000005297 | SEQ ID NO. 5: CCGGGCTGCCAATGGGACAAACATACTCGAGTATGTTTGTCCCATTGGCAGCTTTTT |
| HUMAN RAB27A SILENCER Variant 3: TRCN0000005295 | SEQ ID NO. 6: CCGGCCAGTGTACTTTACCAATATACTCGAGTATATTGGTAAAGTACACTGGTTTTT |

FIGURE 13
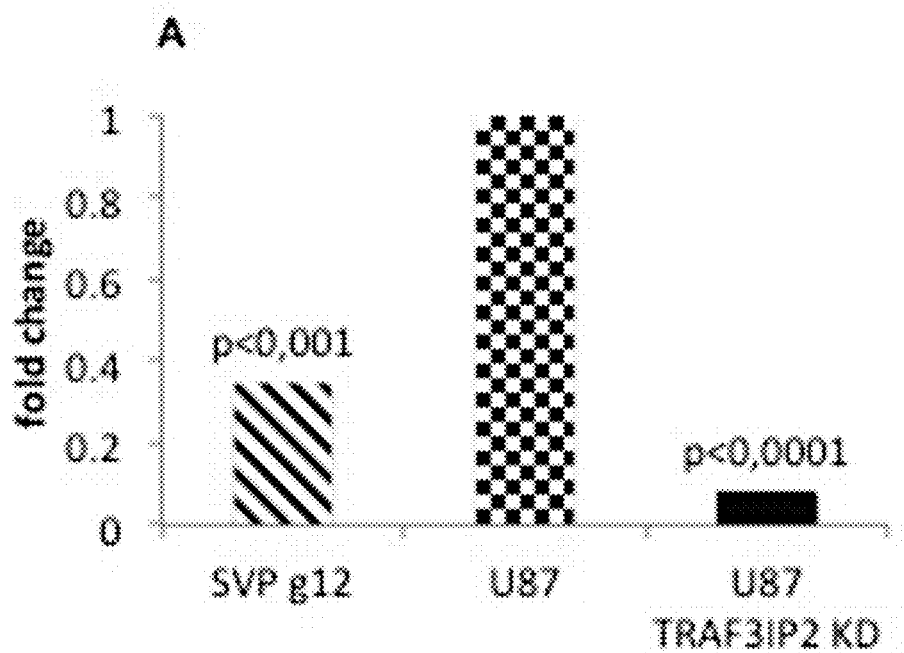
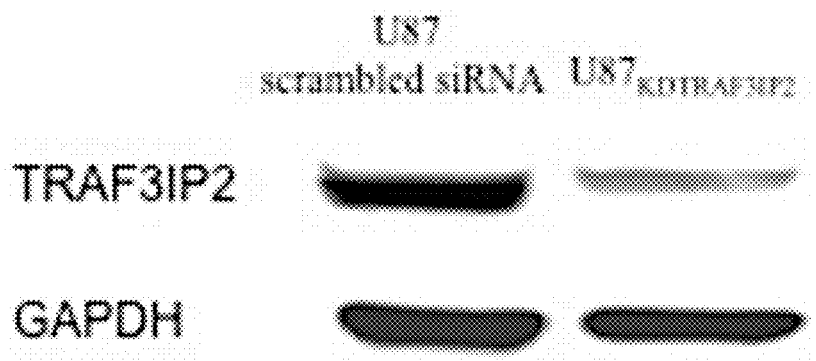

SEQUENCE LISTING

<160> NUMBER OF SEQ ID NOS: 7

<210> SEQ ID NO 1
<211> LENGTH: 58
<212> TYPE: DNA
<213> ORGANISM: Homo sapiens

<400> SEQUENCE: 1
ccggcatgga actatcatta ccattctcga gaatggtaat gatagttcca tgttttttt    58

<210> SEQ ID NO 2
<211> LENGTH: 59
<212> TYPE: DNA
<213> ORGANISM: Homo sapiens

<400> SEQUENCE: 2
ccggccgtga tgataatcgt agcaactcga gttgctacga ttatcatcac ggtttttg    59

<210> SEQ ID NO 3

```
<211> LENGTH: 59
<212> TYPE: DNA
<213> ORGANISM: Homo sapiens

<400> SEQUENCE: 3
ccgggcttca gaacactcat gtctactcga gtagacatga gtgttctgaa gcttttttg      59

<210> SEQ ID NO 4
<211> LENGTH: 57
<212> TYPE: DNA
<213> ORGANISM: Homo sapiens

<400> SEQUENCE: 4
ccggcggatc agttaagtga agaaactcga gtttcttcac ttaactgatc cgttttt       57

<210> SEQ ID NO 5
<211> LENGTH: 57
<212> TYPE: DNA
<213> ORGANISM: Homo sapiens

<400> SEQUENCE: 5
ccgggctgcc aatgggacaa acatactcga gtatgtttgt cccattggca gctttttt     57

<210> SEQ ID NO 6
<211> LENGTH: 57
<212> TYPE: DNA
<213> ORGANISM: Homo sapiens

<400> SEQUENCE: 6
ccgggctgcc aatgggacaa acatactcga gtatgtttgt cccattggca gctttttt     57

<210> SEQ ID NO 7
<211> LENGTH: 6241
<212> TYPE: DNA
<213> ORGANISM: Homo sapiens

<400> SEQUENCE: 7
aatgctgatg tttttaagcag ttagaggagg tggaagaagc tcgactccct cttcttcccc     60
attatctgcc cacaatcccc tcctttggag ctgctaatga ttactaattc ttaacattcg     120
agttcaatct cctcccggag acaccctccc aggcgagggc actgcgacta cactgaggtt    180
ctgcccactc ctgggcagct tcttagctgg gtggcgaaaa caaaaatgcc gcctaattgg    240
tcactggccc tttctcatga atgaaggagg tttctgtttt aagaaataaa gtgactcctc    300
agccgttgat tcactgccca cagggagatt ttgagcagag gcttcctagg ctccgtagaa    360
atttgcatac agcttccact tcctgcttca gagcctgttc ttctacttac ctgggcccgg    420
agaaggtgga gggagacgag aagccgccga gagccgacta ccctccgggc ccagtctgtc    480
tgtccgtggt ggatctaaga aactagaatg aaccgaagca ttcctgtgga ggttgatgaa    540
tcagaaccat acccaagtca gttgctgaaa ccaatcccag aatattcccc ggaagaggaa    600
tcagaaccac ctgctccaaa tataaggaac atggcaccca acagcttgtc tgcacccaca    660
atgcttcaca attcctccgg agacttttct caagctcact caaccctgaa acttgcaaat    720
caccagcggc ctgtatcccg gcaggtcacc tgcctgcgca ctcaagttct ggaggacagt    780
gaagacagtt tctgcaggag acacccaggc ctgggcaaag ctttcccttc tgggtgctct    840
gcagtcagcg agcctgcgtc tgagtctgtg gttggagccc tcctgcaga gcatcagttt    900 tcatttatgg aaaaacgtaa tcaatggctg gtatctcagc tttcagcggc ttctcctgac    960
actggccatg actcagacaa atcagaccaa agtttaccta atgcctcagc agactccttg    1020
```

```
ggcggtagcc aggagatggt gcaacggccc cagcctcaca ggaaccgagc aggcctggat    1080
ctgccaacca tagacacggg atatgattcc cagccccagg atgtcctggg catcaggcag    1140
ctggaaaggc ccctgccct  cacctccgtg tgttacccc  aggacctccc cagacctctc    1200
aggtccaggg agttccctca gtttgaacct cagaggtatc cagcatgtgc acagatgctg    1260
cctcccaatc tttccccaca tgctccatgg aactatcatt accattgtcc tggaagtccc    1320
gatcaccagg tgccatatgg ccatgactac cctcgagcag cctaccagca agtgatccag    1380
ccggctctgc ctgggcagcc cctgcctgga gccagtgtga gaggcctgca ccctgtgcag    1440
aaggttatcc tgaattatcc cagccccctgg gaccacgaag agaggcccgc acagagagac    1500 tgctccttc  cggggcttcc aaggcaccag gaccagccac atcaccagcc acctaataga    1560
gctggtgctc ctggggagtc cttggagtgc cctgcagagc tgagaccaca ggttccccag    1620
cctccgtccc cagctgctgt gcctagaccc cctagcaacc ctccagccag aggaactcta    1680
aaaacaagca atttgccaga agaattgcgg aaagtctta  tcacttattc gatggacaca    1740
gctatggagg tggtgaaatt cgtgaacttt ttgttggtaa atggcttcca aactgcaatt    1800
gacatatttg aggatagaat ccgaggcatt gatatcatta aatggatgga gcgctaccctt   1860 agggataccg tgatgataat cgtagcaatc agccccaaat acaaacagga cgtggaaggc    1920
gctgagtcgc agctggacga ggatgagcat ggcttacata ctaagtacat tcatcgaatg    1980
atgcagattg agttcataaa acaaggaagc atgaatttca gattcatccc tgtgctcttc    2040
ccaaatgcta agaaggagca tgtgcccacc tggcttcaga acactcatgt ctacagctgg    2100
cccaagaata aaaaaaacat cctgctgcgg ctgctgagag aggaagagta tgtggctcct    2160
ccacgggggc ctctgcccac ccttcaggtg gttcccttgt gacaccgttc atccccagat    2220
cactgaggcc aggccatgtt tggggccttg ttctgacagc attctggctg aggctggtcg    2280
gtagcactcc tggctggttt ttttctgttc ctccccgaga ggccctctgg cccccaggaa    2340
acctgttgtg cagagctctt ccccggagac ctccacacac cctggctttg aagtggagtc    2400
tgtgactgct ctgcattctc tgcttttaaa aaaaccattg caggtgccag tgtcccatat    2460
gttcctcctg acagtttgat gtgtccattc tgggcctctc agtgcttagc aagtagataa    2520
tgtaagggat gtggcagcaa atggaaatga ctacaaacac tctcctatca atcacttcag    2580 gctacttta  tgagttagcc agatgcttgt gtatcctcag accaaactga ttcatgtaca    2640
aataataaaa tgtttactct tttgtaagat tatgttttac ttatctcaaa ggagatacat    2700 ataattata  atgatatggg cagttgcttc cagggacatc aacaaagctg cttagatata    2760
atattagata aatataacag accactctgt attaatggat taaagccagc tagttaaaca    2820 accctttta  accataatca tggaagcttt attcttgcaa taaagatttt taggctgggc    2880
gcagtgactc acacctgtaa tcccagcact ttgggaagct aaggcaggca gatcatttga    2940
ggtcaggagt ttgagaccag cctggccaac atggtgaaac cccatctctg ctaaaattac    3000
aaaaaagtta gccgggcatg gtggtgtgca cctgtaatcc cagctactcg ggaggctgag    3060
gcaggagaat cacttgaacc cgggaggcag aggttgcagt gagccgagat catgtcactg    3120
cactctagct gggagacag  agcgagactc cgtctcaaaa aacaaacaaa caaataaaaa    3180
cacccatttt taacaaaaca actttatata gcatacagcc atgattctaa atagtatgat    3240
tatggttctc aggatctgac tacataggta aaaatatttg catatgtgta tgaagtgttg    3300
ggggatgtag gctagaattg tagtctgtgt tctaattttg gttctaccac caattagctg    3360
```

```
tatgaccttt agcaagtcct ttaacttttc ttagattcca gggactcatt tataaaatga    3420
catggacaaa agcatctcta atcactctaa aagatttgaa gtctaggacc taaattctaa    3480
atactctttt gaggagtgac tgagttttca ttttcataat tatgtctctc agaggacaaa    3540
tttacatttt cttaacagag acatttttctt cttcttttttt tttgtttgag acagagtctc    3600
gctctgtcgt ccaggctgga gtgcagtgct gcaatcttgg ctcactgcaa cctgcgcctc    3660
ctgggttcaa gtgattcttc tgcctcaacc tcccaagtag ctagacctat aggcgcctgc    3720
caccatgccc agctaatttt tgtattttta gtagagacag ggtttcatat tggccagact    3780
ggtctcgaac tcctgacctt gtgatccgcc cacctcggcc tcccaaagtg ctgggattac    3840
aggtgtgagc caccacaccc agccaacatt ttcctctttt aaaaaatatc ttctcacgcc    3900
tgtaatccca gcactttggg aggctgaggc aggcggatca tgaggtcagg agatcaagac    3960
catcctggct aacacggtga aactccatct ctactaaaaa tacaaaaaaa atagccgggc    4020
gtggtggcag cgcctgtag  tcccagctac tggggaggct gaggcaggaa aatggtgtca    4080
acccgggagg cggagcttgc agtgagccga gattgcgcca ctgcactcca gcctgggcaa    4140
tagagtgaga ctccgtctca aaaaaaaaaa aaaaaaaaa aacttcaaca ataccctcag    4200
gttgataatt ttggatatct atctgtatct atatatcttg tttacctggt ctccagaaaa    4260
agaacacata cacatatcca tatataaaat atgtatacat gtatcaaatc tacgtaaact    4320
ataaaggtgg gatggcttta attatggccc aagctactaa gacaatgaag acttttttggg    4380 gctgcaagct actgcttccc ttctttatct actagcctct taaacaaggc tcacttgtgc    4440
tacaagacag tccaccgttt tgtttttttt ttctttttttt tgagacaggg tctcactctt    4500
tcccaggctg cagtacagtg acacagtctc agctcactgc agctttgacc ttgccgggct    4560
caggtgaccc ttacacttca gcctcccaag tagcagggac tataggtgtg caccaacatg    4620
cttggttaat ttttgtattt tttgtagaga cagggttttg ccatgttgtc caggctagtc    4680
tcgaattcct gggctcaagt gattcacctg ccttggcctc ccaaagtgct aggattacag    4740
atgggagcca ccacgcccag cccagtccag ctcttatatg tagcacaggg aaaggacaaa    4800
tacttgtcaa ctataaataa gaaacattgc taatgcattg caaagaacac tagtttcatt    4860
tactttataa cttagatgtc tactgggtga gacgaatgtc tttgttcttt aaaaaatagg    4920
aaaagagaag aaaaactagc ataacataag tactcatttg taagactttc tgacatgtaa    4980
cattagttcc gtagttttga gacctggtag aactgacttt catatttgga taacctggaa    5040
aacacccaaa cacaaacttc aagtcttctt tctcttttttt cattatcttt tttagtctga    5100
ggtgacacca tcattaagga ttcgacaccc gtttgtaaat aaaatgacat cagcaattac    5160
tctgaaatgt ttctagtttg caaagactta gcaatgtgat gttattaacc cttcctccct    5220
tcagagacct gtcctaagct ctgaaccact cattccttcc actcttctta ccccaggtgg    5280
ttgatgagca gtggtccctg tgttccaca  aagagtcatt aaagtgttac agctggtagc    5340
actggtagca aaaaaacaaa ccaaaaagta cacacagaca cacacacaca cacgcacaca    5400
tacacacaca cacgcacttg gccaagtgac aaaagcttgg cccctgaaat ttctatgaga    5460
tccgatgacc accaacatca aagcattttt tttttttttt ttttgagacg tagtctcgct    5520
ctgtcaccca ggctagagtg cagtggtgca atcacagctc actgcaacct ccacctcccg    5580
ggttcaagcg attctcctgc ctcagcctct cgagtagctg tgactacagg cacctgccac    5640
catgcccggc taatttttttg tattttttagt agagacgggg tttcaccgtg ttagccagga    5700
tggtcttgat ctcctgacct cgtgatccat ccgcctcggc ctcccaaatt gctgggatta    5760
```

-continued

```
caggcatgag ccaccacgcc cggcccatca aaggaattgt aacaactatt tgagagcact    5820
gacaataaga ttaacactcg gttgatttag atgttatgct ggtcctcagg cattcatctt    5880
tagatatttt tggggtggaa gtggggtagg gctgacttag taaaaataac ctcttagccc    5940
aaaggcttta ttcagactta caccgatttg aggggtgggt ttgtggaatg caaggttagg    6000
ttcttaccta atatttgatg actaatttag aattttaaat gtaattttaa attttagtga    6060
ctggtttcaa atctatttta acttctagat tgttcaaaga ggtctcagta catggctaca    6120
atcaaagtat tagactagct atttctcagc tcagtgctca gaaaaattat tactgttgat    6180 accttttct ttgtttcctg ttaaataaat cacctcttta aagacagaaa aaaaaaaaaa    6240
a                                                                   6241
```

PREVENTING TUMOR DEVELOPMENT AND METASTASIS

CROSS-REFERENCES TO RELATED APPLICATIONS

This application claims priority to U.S. Ser. No. 62/031,021, filed Jul. 30, 2014, incorporated by reference herein in its entirety for all purposes.

STATEMENT REGARDING FEDERALLY SPONSORED RESEARCH

Not applicable.

FIELD OF THE INVENTION

The present invention relates to novel methods to prevent tumor metastasis and suppress tumor growth, especially of solid tumors, by interfering with tumor communication and its environment and by impacting the formation and development of the tumor microenvironment.

DESCRIPTION OF RELATED ART

Tumor development occurs following the accumulation of genetic and epigenetic alterations in tumor cells. It has been demonstrated that tumor growth is strongly influenced by non-malignant cells that together with the tumor cells form the tumor microenvironment. Numerous reports have revealed the complexity of the communication between tumor cells and the heterogeneous population of stromal cells within the tumor microenvironment.

For example, the tumor-stromal cell interactions have a crucial role in tumor initiation and progression. These stromal cells, including fibroblasts, myofibroblasts, endothelial cells, mesothelial cells, adipocytes, tissue resident stem cells, and immune cells, are involved in tumor development via several mechanisms including:
  (i) cell-cell and cell-matrix interactions influencing cancer cell sensitivity to apoptosis;
  (ii) local release of soluble and genetically modifying factors promoting survival and tumor growth, growth of tumor blood vessels and resistance to attack by the patient's immune system (crosstalk between stromal, immune cells and tumor cells);
  (iii) direct cell-cell interactions with tumor cells (crosstalk or oncologic trogocytosis);
  (iv) generation of specific properties and niches within the tumor microenvironment that facilitate the acquisition of drug resistance; and
  (v) conversion of cancer cells to cancer-initiating cells or cancer stem cells.

These interactions between malignant and non-malignant cells modify cellular compartments, leading to the co-evolution of tumor cells and their microenvironment.

Although the importance of microenvironmental alterations in tumor development is recognized, the molecular mechanisms underlying these changes are only now beginning to be understood. Detailed molecular characterization of various cell types from normal breast tissue, ductal carcinoma, and invasive breast tumors has revealed that gene expression changes occur in all cell types during breast tumor progression.

Recently, it has been shown that, in addition to bone marrow-derived MSCs, adipose tissue-derived MSCs display significant affinity to tumor microenvironment. The role of inflammation in the tumor microenvironment is crucial in the pathology of cancer because it regulates the directional movement of tissue resident immune cells and stem cells.

Although decades of research have yielded targeted therapies that are effective in eliminating or reducing some tumors, breast cancer remains the leading cause of morbidity and second-leading cause of death in women. Recent published reports suggest that reciprocal influences exist between breast tumor cells and the tumor microenvironment and that these interactions affect the growth and energetics of the tumor. These interactions reveal the contributions of individual cells within a tumor to the overall disease. In addition, a neurological tumor such as glioblastoma multiforme is even more malignant and the 5-year survival rate of patients diagnosed with such a tumor still is below 5%.

The present invention provides novel compositions and methods to affect the interactions between a tumor and its microenvironment to prevent, reverse, and/or reduce tumor growth and metastasis.

BRIEF SUMMARY OF THE DISCLOSURE

The present disclosure provides novel therapies for tumors, especially solid tumors, such as breast cancers or glioblastomas, by interfering with tumor communication with the tumor environment and/or by regressing formation of the microenvironment, thereby preventing or reversing tumor metastasis and suppressing tumor growth. In a preferred embodiment, the present invention discloses a cancer therapy by silencing TRAF3IP2 and/or RAB27A expression.

Silencers can be delivered to a tumor in a number of ways, including at least:

1) Delivering silencing RNA by injecting an expression vector encoding the silencer to the tumor site, e.g., directly into a tumor site under visual, ultrasound, fluoroscopy, CT or MRI guidance or other imaging modalities, or indirectly through blood vessels or ducts that lead to the tumor.

2) Use of silencing RNA delivered by tumor targeting cells, such as migratory stem cells, e.g., MSCs, that due to their nature preferably migrate and engraft to the tumor site. Such cells would contain therein either an expression vector or a genomic copy of the sequence encoding the silencer.

3) Delivering encapsulated or otherwise protected silencing RNA to the tumor site. The silencing RNA is for example encapsulated into microspheres (i.e. exosomes) or micelles, liposomes and the like. The microspheres will be delivered by direct or indirect injection to the tumor site either trough a transcutaneous injection or through a vessel or duct supplying the tumor site. Preferably, such RNAs will be RNAse resistant, and if so, naked RNA may be used.

4) Silencing RNA linked to a specific tumor directed antibody or protamine coupled construct to increase the tumor specific concentration and to enhance the local effect of the silencing RNA within the tumor site.

5) Achieving a selective effect targeting the tumor cells and virtually avoiding an effect on non tumor cells by i) increasing the local concentration within the tumor by selective delivery means as described above, ii) by the fact that the respective genes of TRAF3IP2 and of Rab27a are ten to thirty times (respectively) upregulated in tumor, especially in tumor stem cells, compared to normal stem cells, and iii) the silencer is released in a (transactivator)-inducible manner (such as IL1B), thus expression is activated mainly in the tumor.

6) Combinations and variations of the above.

Silencing TRAF3IP2 in tumor cells confines cytokine expression and ultimately limits the development of the tumor microenvironment. This eventually slows or prevents tumor growth and restrains tumor metastasis. The tumor cells exhibit significantly higher levels of exocytosis activities compared to non-malignant cells.

Two alternative transcripts of TRAF3IP2 encoding different proteins have been identified. A third transcript, which does not encode a protein and is transcribed in the opposite orientation, has also been identified. Overexpression of this transcript has been shown to reduce expression of at least one of the protein encoding transcripts, suggesting it has a regulatory role in the expression of this gene and indicating its use in the methods described herein.

For the actual silencer sequence used in our proof of concept studies, we used commercially available silencers (SIGMA ALDRICH®) RNA to target TRAF3IP2 and RAB27A either separately or in combination. However, any type of silencer for these genes could be used.

Basic design rules for the various types of silencers are available, and once designed the silencers can be tested for efficacy according to the methods discussed herein and in the literature.

For example, a short hairpin silencer (shRNA) generally has about 18-30 nucleotides (nt), preferably 21 nt, comprising a unique sense strand of target mRNA beginning with AA linked to a loop (3-9 nt) linked to an complement of the unique sense strand and finishing with polyT, thus forming a hairpin. An initiating G nt could also be used.

Another type of silencer, is the siRNA of about 18-30 nt, preferably 21 nt, comprising a unique sense strand of the target mRNA beginning with AA and finishing with polyT.

Another type of silencer is the antisense sequence. These can be a unique antisense sequence from the target, or an RNAse resistant 18-30 nt antisense RNA sequence from the target. Effective antisense silencers may also be located in exons, but close to the acceptor splice site (SS).

miRNAs generally work when about 21-23 nt and have complementarity maintained in the first third of the small RNA and target mRNA, but mismatches arise in the remainder of the aligned sequence.

The above rules are guidelines only, however, and there is certainly variability in approaches. Therefore, it is typical to design 4-6 such silencers using the basic rules and then test each for activity, e.g., in an ex vivo system. Therefore, given the validity of the target, silencers can be readily be designed using the target sequence.

In addition, validated silencers for several genes are already commercially available. LIFE TECHNOLOGIES® for example has 27 validated silencers (6 human) for TRAF3IP2, and 9 for RAB27A (3 human). SIGMA-ALDRICH® also provides several shRNAs and siRNAs for use, including the human TRAF3IP2 silencer MISSION® shRNA Lentiviral Transduction Particles (SHCLNV-NM_147200) and the human RAB27a silencer MISSION® shRNA Lentiviral Transduction Particles (SHCLNV-NM_004580). In addition, Sigma offers miRNA mimics, and esiRNA. Furthermore, the RNAi Consortium has built a library of shRNAs directed against 15,000 human and 15,000 mouse genes.

Furthermore, silencer RNAs can be stabilized against nucleases by incorporating modified bases therein, such as methylphosphonate, phosphorothioate, α-nucleoside, 2'-O-substituted RNA, phosphoramidite, morpholino and chimeras contain an internal core of unmodified phosphodiester RNA/RNA flanked by modified residues. These can be very useful where naked or encapsulated nucleic acid is directly delivered, as opposed to an expression vector encoding the silencer.

We have specifically targeted breast cancer and glioblastoma cell lines herein for proof of concept experiments, but we anticipate that the method can be used in many cancers or inflammatory conditions since TRAF3IP2 and/or RAB27A play a role therein. The TRAF3IP2 gene, for example, is implicated in several cancers, including lung cancer, colon cancer, cervical cancer, endometrial cancer, liver cancer, ovarian cancer, prostate cancer, stomach cancer, testis cancer, thyroid cancer, carcinoid tissue, urothelial cancer, pancreatic cancer, sarcomas, melanoma and the like. See e.g., proteinatlas.org/ENSG00000056972-TRAF3IP2/cancer. It is also implicated in inflammatory bowel disease, atopic dermatitis, psoriasis, Hodgkins disease, familial candidiasis, possibly ulcerative colitis, and the like. Any cancer with at least 5 or 10 fold or higher higher levels of either of these transcripts can be used in the methods herein.

RAB27A mainly regulates exocytosis, and thus silencing RAB27A attenuates exocytosis. The lower exocytosis limits the release of oncogenic molecules into the tumor microenvironment in both soluble and insoluble forms. This ultimately restricts the development of tumor microenvironment.

RAB27a is known to be highly expressed in some cancer as well, including pancreatic cancer, breast cancer, colorectal, lymphoma, prostate, melanoma, ovarian, thyroid, and the like.

While there are several methods of delivering silencers to tumors, one preferred method uses of mesenchymal stem cells or "MSCs". Using their known preferred tumor homing capacity, MSCs are modified with a vector expressing the respective silencing sequence. Silencing vectors are thus delivered to the tumor site foci using these MSCs that produce the respective silencing RNA against TRAF3IP2, Rab27a, or against both. In addition and as a means to increase the effect on tumor cells and minimize the effect on non-tumor cells, tumor-tropic subset of MSCs that are obtained and identified by their preference to migrate towards the tumor cells can be used. They can be created by prior exposure to exosomes that induce the needed epigenetic changes in the MSC or by selecting by FACS sorting MSCs expressing specific tumor surface markers, such CXCR4, or the PDGF bb receptor.

The tumor-tropic MSCs carrying therapeutic vectors will home to the vicinity of tumor cells and then express the silencers in the tumor microenvironment where there is higher expression of IL1B, if we use an IL1B inducible promoter herein. The silencer is thus released and reduces tumor-related inflammation and tumor size with minimal off-target effects since healthy tissue won't have high levels of IL1B. The MSCs containing silencing vector ($5 \times 10^5$/subject) are administered systemically, e.g., by injection into the bloodstream, into a local tumor supporting blood vessel or duct, or directly transcutaneous into the primary tumor or its metastasis.

Although we have used MSCs as delivery vehicles herein, this is an continually evolving area of research and another method may ultimately emerge as more preferred over the course of research. Other possible delivery vehicles include Rexin-G, an engineered retroviral nanoparticle that achieves targeting to cancerous lesions through the attachment of a collagen motif that binds to "newly exposed" extracellular matrix, which is typically associated with tumor tissue. Another possibility is to use a virus engineered to target a particular cancer cell, such as the parvo virus H1, or to link the silencer with tumor specific ligand or antibody.

There are also non-viral methods of silencer delivery, including e.g, injecting naked DNA/RNA into a tumor, injected protected RNA into tumors, electrotransfection, the use of polymers, liposomes, and the like, to protect the nucleic acids, or to stabilize the silencer through linking it to Protamin.

Lentiviral vectors were used herein to encode the silencer sequences for TRAF3IP2 and RAB27A. Although data show that there is specificity for CD45+ cells transduction in vivo when administering lentiviral vectors, MDA-MB231 and SW620 cells are highly transducible with lentiviral vectors. Thus, these vectors were useful for proof of concept studies. However, any suitable expression vector may be used herein, or the gene can be introduced into the genome of a homing cell (e.g., by homologous recombination), such as the MSCs discussed herein.

Common vectors are based on herpes simplex type 1 recombinant vector (HSV-1); adenovirus, adeno-associated viral vector (AAV); alpha virus; vaccinia virus; pox virus; sendai virus; plasmids; retrovirus; ssDNA vectors; and the like. To date, adenovirus, retrovirus and naked plasmid DNA have made up more than half of the vectors tested in clinical trials of various gene therapies.

An IL1B transactivator-inducible system is a preferred promoter for use in our lentiviral vector. The IL1B promoter activates the expression of silencer RNA by binding the endogenous IL1B, which is highly produced by cells within tumor microenvironment. However, this promoter is exemplary only and there are many to choose from, including several antibiotic resistance or drug responsive promoters that can be safely used in humans (e.g., tamoxifen, tetracyclin, ampicillin and the like).

The disclosure provides one or more of the following embodiments, in any combinations(s) thereof:

A pharmaceutical composition for the treatment of a tumor, wherein said composition comprises at least one silencing sequence for TRAF3IP2 or RAF27A or both in a pharmaceutically acceptable nucleic acid carrier in an amount effective for the therapeutic treatment of a tumor.
A silencing sequence for TRAF3IP2 or RAF27A or both for use as a medicament, or for use in treating a tumor, or solid tumor, or for use in treating glioblastoma or breast cancer, or for use in treating any cancer with at least 5-10 fold increased TRAF3IP2 and/orRAB27a expression.
A use of a silencing sequence for TRAF3IP2 or RAF27A or both for the manufacture of a medicament for the treatment of a tumor or solid tumor, or for use in treating glioblastoma or breast cancer, or for use in treating any cancer with at least 5-10 fold increased TRAF3IP2 and/or RAB27a expression.
A pharmaceutical composition for the treatment of a tumor, wherein said composition comprises an expression vector encoding a TRAF3IP2 silencer operably coupled to an inducible promoter in a pharmaceutically acceptable nucleic acid carrier.
A pharmaceutical composition for the treatment of a tumor, wherein said composition comprises an expression vector encoding a RAF27A silencer operably coupled to an inducible promoter in pharmaceutically acceptable nucleic acid carrier.
A pharmaceutical composition for the treatment of a tumor, wherein said composition comprises at least one expression vector encoding a TRAF3IP2 silencer operably coupled to a first inducible promoter and a RAF27A silencer operably coupled to a second inducible promoter in pharmaceutically acceptable nucleic acid carrier. The first and second inducible promoters can be the same promoter or different.
Any composition herein described, wherein said silencer is an siRNA, an shRNA, an miRNA, or an antisense.
Any composition herein described, wherein said silencer comprises any sequence herein referenced or described.
Any composition herein described, wherein said expression vector in a mesenchymal stem cell (MSC) that targets said tumor. Preferably, the MSCs have been exposed to exosomes from said tumor.
Any composition herein described, wherein said composition comprises a product for parenteral administration including direct injection into a tumor or its metastasis site by transcutaneous, intraarterial, intraductal, intravenous, intradermal, intramuscular, and subcutaneous administration.
A method of treating at least one tumor in a mammal comprising administering to the mammal an effective amount of any composition herein.
A method as herein described, wherein said tumor is a human breast cancer or a glioblastoma or any cancer with at least 5X increased TRAF3IP2 and/or RAB27A levels, or at least 10 fold, or at least 20 fold or at least 30 fold.
A method as herein described, wherein the composition is injected directly into said tumor and said injection is guided by ultrasound, fluoroscopy, imaging, CT, MRI, or just visually in order to enhance the local concentration of the silencer within the tumor.
A method of treating a tumor comprising administering a silencer for TRAF3IP2 or RAB27A or both to a patient having a tumor in an amount effective to slow or reverse said tumor growth, said silencer comprising:
about 18-30 nucleotides (nt) RNA comprising a unique sense strand of NM_001164281.2 or NM_004580.4 beginning with AA linked to a hairpin loop linked to a complement of said unique sense strand and ending with polyT;
about 18-30 nt RNA comprising a unique sense strand of NM_001164281.2 or NM_004580.4 beginning with AA and ending with polyT;
a unique antisense RNA sequence from NM_001164281.2 or NM_004580.4;
an RNAse resistant 18-30 nt antisense RNA sequence from NM_001164281.2 or NM_004580.4; or
about 21-23 nt RNA copy of NM_001164281.2 or NM_004580.4 having complementarity maintained in the first third of the RNA, but mismatches in the remainder of the RNA.
A method as herein described, wherein said silencers are about 21 nt.
A method as herein described, where said silencer is RNAse resistant.
A method as herein described, wherein said silencers are delivered to said breast tumor by an expression vector.

| |
|---|
| A method as herein described, wherein said silencers are encoded by expression vectors contained inside MSCs. |
| A method as herein described, wherein said silencers are delivered to said tumor by injection. |
| A method as herein described, wherein said silencers linked to an antibody targeting a breast tumor specific cell surface antigen. |
| A method to selectively treat a tumor and minimize side effects, by administering an effective amount of a silencer for TRAF3IP2 or Rab27a, or both, to a tumor that expresses at least 10 times the amount of TRAF3IP2 or Rab27a, or both, as compared to a non-tumor cell from the same tissue. |
| A method as herein described, further comprising enhancing the selective effect on tumor cells and avoiding effects on normal cells by increasing the local concentration of the silencer within the tumor by injecting said silencer(s) directly into said tumor. |
| A method as herein described, wherein said silencer(s) is encoded in an expression vector having an inducible promoter, thus enhancing the selective effect on tumor cells and avoiding effects on normal cells by means of selectively activating the production of the silencer by a switch that activates said inducible promoter. |
| A method as herein described, wherein said switch is preferentially or only found in said tumor. |

As used herein, the term "expression vector" means a DNA or RNA into which a sequence of interest can be inserted that operably linked to a promoter such that the sequence will be transcribed or expressed from the promoter in the host cell/animal of interest. Thousands of such vectors are available. See e.g., Addgene.org which provides both a repository and a searchable database allowing vectors to be easily located and obtained from colleagues. See also Plasmid Information Database (PlasmID) and DNASU having over 191,000 plasmids. A collection of cloning vectors is also kept at the National Institute of Genetics as a resource for the biological research community. Furthermore, vectors (including particular ORFS therein) are usually available from colleagues.

As used herein, the term "silencing" refers to the down-regulation of gene expression. At least 65%, 70%, 75%, 80% reduction should be achieved, but preferably, this term refers to the ability of a cell to prevent the expression of a certain gene. Gene silencing can occur during either transcription or translation and is often used in research and gene therapies.

By "preventing" gene expression, we mean no detectable intact gene expression is detected when assayed by Northern blot using a radioactively end-labeled oligomer that is complementary to the gene being silenced. Nonetheless, there may be minute amounts of expression that could be detected by extremely sensitive methods.

The term "silencer" as used herein refers to a exogenous sequence that can be introduced into cells and used to silence gene expression in that cell. There are several different types of silencers, including at least antisense oligonucleotides, ribozymes, RNA interference, and the like. Genes can be silenced by e.g., dsRNA that decomposes mRNA, siRNA molecules that cause the endonucleatic cleavage of the target mRNA molecules or by miRNA molecules that suppress translation of the mRNA molecule or by shRNA, as well as by endoribonuclease-prepared siRNAs (esiRNAs), which are a mixture of siRNA oligos resulting from cleavage of long double-stranded RNA (dsRNA) with an endoribonuclease such as *Escherichia coli* RNase III or dicer. The term "silencer" is not limited to any one particular methodology, unless so specified.

By "exosomes" what is meant herein are cell-derived vesicles that are present in many and perhaps all biological fluids, including blood, urine, and cultured medium of cell cultures.

As used herein, the expressions "cell", "cell line" and "cell culture" are used interchangeably and all such designations include progeny. Thus, the words "cells" and similar designations include the primary subject cell and cultures derived therefrom without regard for the number of transfers. It is also understood that all progeny may not be precisely identical in DNA content, due to deliberate or inadvertent mutations that arise after genetic engineering is concluded. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" is relating to, derived from, or containing genetically "engineered" material. In other words, the genome was intentionally manipulated by the hand of man in some way.

"Reduced activity" or "inactivation" is defined herein to be at least a 75% reduction in protein/gene activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like. A negative superscript, as in $ACT1^-$, indicates reduced activity.

As used herein the specification, "a" or "an" may mean one or more. As used herein in the claim(s), when used in conjunction with the word "comprising", the words "a" or "an" may mean one or more than one. As used herein "another" may mean at least a second or more.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

Wherever any of the phrases "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The disclosure may use one or more of the following abbreviations:

| Abbreviation | Meaning |
| --- | --- |
| ASC | Adipose tissue derived stem cells |
| bi-shRNA | bifunctional shRNA |
| esiRNA | Endoribonuclease-prepared siRNAs |
| GFP | Green fluorescent protein |
| KD | Knock down (refers to silencers herein) |
| miRNA | microRNA |
| MSC | Mesenchymal stem cells |
| RAB27A | RAS-ASSOCIATED PROTEIN 27A (UniProt P51159) |
| RFP | Red fluorescent protein |
| RNAi | RNA interference |
| shRNA | Small hairpin RNA |
| siRNA | Small interfering RNAs |
| TRAF3IP2 | TRAF3-INTERACTING PROTEIN 2 aka NUCLEAR FACTOR KAPPA-B ACTIVATOR 1 or ACT1 (UniProt O43734) |

BRIEF DESCRIPTION OF THE DRAWINGS

FIG. 4A shows the expression of TRAF3IP2 and RAB27A in cultures of MDA-MB231, 184A1 and MSCs. The expression of both TRA3IP2 and RAB27A are significantly higher in MDA-MB231 cells than in 184A1 and MSC cells. The co-cultures of 184A1 and MSCs with MDA-MB231 cells enhanced the expression of TRAF3IP2 and RAB27A in both 184A1 and MSCs.

FIG. 4B Using silencing RNA, the expression of TRAF3IP2 and RAB27A were silenced in MDA-MB231, 184A1 and MSCs. The doubling time was calculated and compared to wild type cells. The silencing of RAB27A and TRAF3IP2 decreases the proliferation of MDA-MB231 cells, while having no effect on MSC replication capacity.

FIG. 4C Using a protein array technique, the cytokines released in culture media (CM) of MDA-MB231 and $MDA_{KDTRAF3IP2}$ cells were assessed. Cytokine array analysis shows that the level of cytokines mostly involved in breast cancer progression and metastasis are significantly reduced in $MDA_{KDTRAF3IP2}$ cells (n=3; P<0.05).

FIG. 6 demonstrates altering tumor microenvironment formation in vivo. A. $1 \times 10^5$ $MDA_{KDTRAF3IP2}$ and $MDA_{KDRAB27A}$ cells in PBS and Martigel were injected intra-mammary in NIHIII female mice (4-6 weeks old). As controls, a group of animals were injected with $1 \times 10^5$ MDA-MB231 cells in PBS and Martigel, another group was injected with Martigel, and another group was injected with PBS (n=15/group). Tumor growth was measured, and control animals injected with MDA-MB231 cells were euthanized 8 weeks post-injection. Animals injected with $MDA_{KDRAB27A}$ cells were euthanized 30 weeks post-injection for further analysis. $MDA_{KDTRAF3IP2}$-injected animals showed minimal tumor growth and were euthanized on week 52 of injection for further analysis. B shows a graph illustrating the survival of animals injected with MDA-MB231, $MDA_{KDTRAF3IP2}$ and $MDA_{KDRAB27A}$ cells (P<0.05).

FIG. 8 shows the sequence of several silencer sequences, or provides an accession number for same.

FIG. 13 shows TRAF3IP2 gene (A) and Protein (B) expression levels. Wild type U87 were transduced with is scrambled silencer RNA (SVg12) and used as control in these experiments. Scrambled shRNA is a non-target silencer RNA, which is used as a control in these experiments.

DETAILED DESCRIPTION OF THE DISCLOSURE

Figure 1:
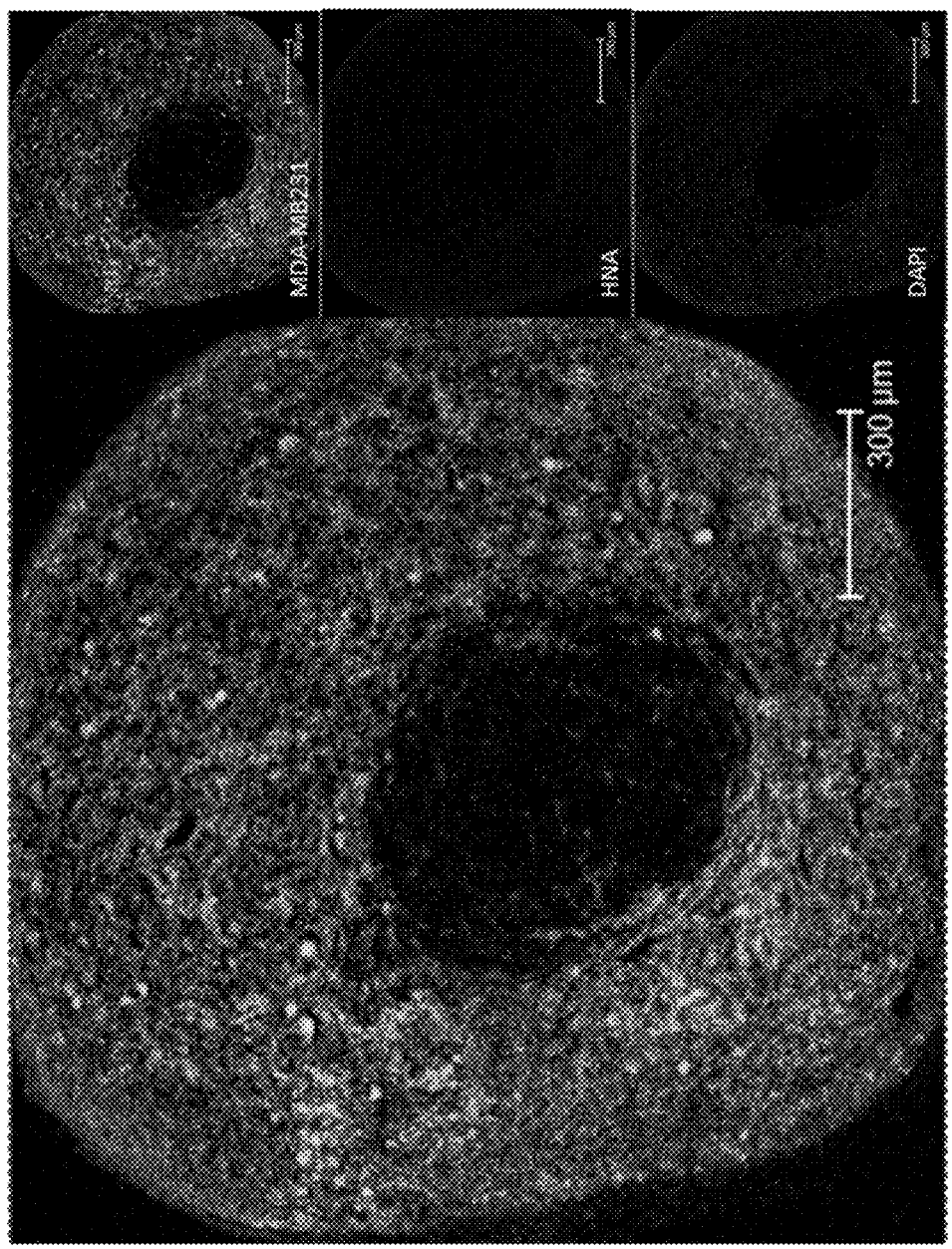
FIG. 1 shows the localization of MSCs in tumor location. MDA-MB231 of genetically modified GFP expressing cells were injected intra mammary in 4-6 week old NIHIII immune-deficient female mice (n=5). $5 \times 10^5$ MSC cells were injected into the tail vein of these animals, which were euthanized 7 weeks post injection. The tumor tissues were extracted, fixed, and subjected to immunohistochemistry using HNA antibody to detect the human cells and DAPI for staining DNA. The samples were imaged with Leica confocal microscope (10×).
Figure 2:
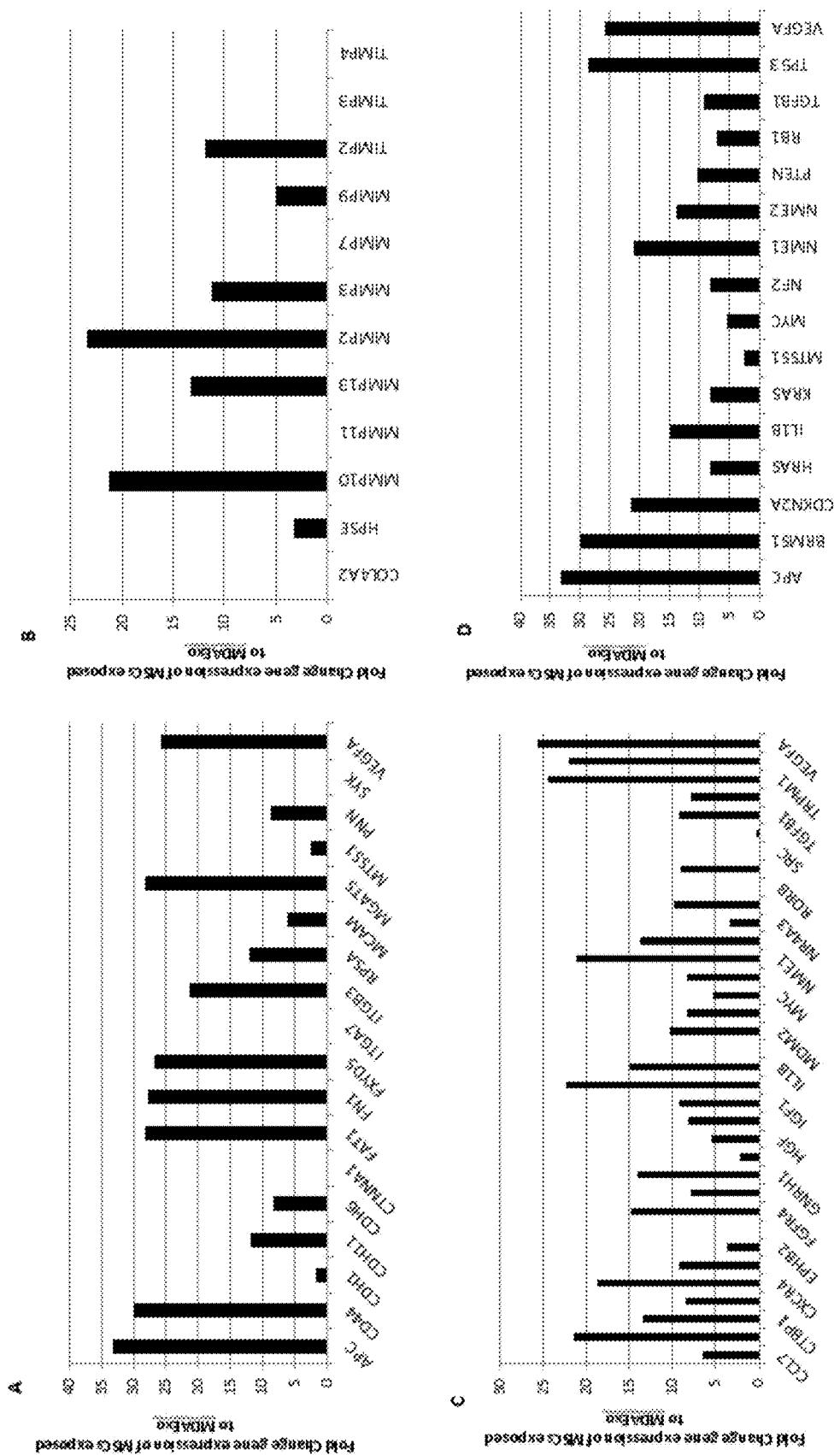
FIG. 2 shows the effect of exosomes on the gene expression of MSCs. To study the effect of exosomes on MSCs' gene expression, MSCs were incubated with purified exosomes derived from MDA-MB231 cells ($MDA_{Exo}$) for 14 h in 37° C. and 5% $CO_2$. The changes in gene expression in MSCs were assessed using PCR array. The perturbed genes that displayed greater than two fold changed expression were grouped based on their function of cell adhesion (A), extracellular matrix proteins (B), cell growth and proliferation (C), and cell cycle (D). The graphs are representatives of triplicate experiments (P<0.05).

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Furthermore, while the invention is exemplified in breast cancer cell lines injected into mice with particular vectors and silencers, this is for proof of concept only, and the methods are expected to work in many different tumors with a variety of silencer delivery methods and with a variety of silencer sequences.

The following materials were used herein:

| | |
|---|---|
| MDA-MB231 cells | A human breast cancer cell line, available from Sigma-Aldrich ® |
| MDA$_{KDTRAF3IP2}$ cells | MDA-MB231 cells transformed with a lentiviral vector encoding a TRAF3IP2 silencer. |
| MDA$_{KDRab27}$ cells | MDA-MB231 cells transformed with a lentiviral vector encoding RAB27A silencer |
| 184A1 cells | A human mammary gland cell lines, established by chemical transformation (ATCC ® CRL-8798) |
| Lentiviral vector | A lentiviral-based vector (e.g. pLKO.1-puro or pLKO.1-puro-CMV-TurboGFP™), preferably having a transactivator inducible promoter, such as IL1B promoter which will be activated in presence of excessive amounts of IL1B within tumor microenvironment. |
| U87 | U87 is a human primary glioblastoma cell line formally known as U-87 MG. It has epithelial morphology, and was obtained from a stage four 44 year-old cancer patient, and can be obtained from ATCC (HTB-14). |
| SVg12 | SVg12 is scrambled silencer RNA construct in a lentiviral vector that functions as a control for transduction in these experiments. |

Exosomes

Exosomes are the main insoluble components of the tumor microenvironment. Exosomes are small membranous extracellular vesicles (40-100 nm in diameter) that are released in extracellular space. In addition to production by tumor cells, exosome-like vesicles are produced by various non-malignant cell types. Structurally, these vesicles consist of a lipid bi-layer membrane similar to the cellular membrane, proteins, including host specific proteins, mRNA, and microRNA (miRNA).

Exosomes can affect various cell types by transferring their content to various cells. The growing interest in the characterization of exosome-like vesicles in cancer research arises from their potential role in carrying a large array of oncogenic elements released by malignant cells, such as oncogenic proteins and miRNAs. Such oncogenic proteins and miRNAs can traverse the tumor microenvironment and can be taken up by recipient non-malignant cells; this can result in the transfer of oncogenic activity.

It has been shown that the release of exosomes into extracellular spaces is through exocytosis. RAB27A is one of the exocytosis regulators. RAB27A, a membrane-bound protein, is thought to be important for directing secretory lysosomes to the immunologic synapse and for their release from microtubules. At the membrane, RAB27A is activated by exchange of bound nucleotide GDP for GTP. Active RAB-GTP then recruits effector proteins from the cytosol to the membrane. These are a diverse group of proteins that include lipid kinases and phosphatases, molecular motors, and tethering factors, which are involved in protein transport and small GTPase mediated signal transduction.

A tumor can neither grow nor metastasize without the development of supporting stroma. In solid tumors, the associated stroma consists of a mixture of several cell types, cytokines, chemokines, and extracellular exosome-like vesicles. These accumulations change the function and composition of tissue surrounding the cancer cells and form the tumor microenvironment. As noted above, the tumor microenvironment contains both cellular and acellular fractions. The acellular fraction, consisting mainly of soluble inflammatory cytokines and insoluble extracellular exosomes-like vesicles, is involved in tumor-related inflammation and growth. Tumor cells take part in releasing both cytokines and exosomes into the tumor microenvironment via exocytosis. Exocytosis is a cellular process that directs the contents of secretory vesicles out of the cell membrane and into the extracellular space. This process is regulated mainly by the function of the RAB27A gene.

Mesenchymal stem cells (MSCs) are a type of stromal cells abundant in the tumor microenvironment. MSCs have been identified in several tissues. Adipose tissue and bone marrow have been described among the major sources of MSCs in adults. MSCs resemble fibroblasts in terms of shape and markers; they are capable of self-renewal and contribute to tissue regeneration by differentiation into osteoblasts, chondrocytes, adipocytes, myocytes, macrophage-like cells and myofibroblasts, depending upon the requirements of the site to which they are recruited.

MSCs have been found to be incorporated into tumors as well as in inflammatory milieu, such as healing wounds. In tumor biology, the homing of MSCs to tumors is the most significant hallmarks of these cells. Several reports have indicated that MSCs are capable of homing to the tumor site, but results of current studies investigating the signals that recruit MSCs to developing tumor sites are controversial. During the normal homing process, which is common to both hematopoietic stem cells (HSCs) and MSCs, the cells migrate from their locations via proteolysis and are directed to a particular injury site. Reports indicate that MSCs are recruited to tumor sites in the same fashion. This tropism of MSCs has been exploited for gene therapy and delivering drugs in a targeted way to the tumor site, and we have also used this tropism herein.

A recently published report described the effect cytokines exert in recruitment of MSCs to the tumor site in breast cancer (Senst, Nazari-Shafti et al. 2013). It also showed that co-culturing MSCs and MDA-MB231 cells (MSC+MDA-MB231) enhances the expression of cytokines from tumor cells. GRO-α, IL6, IL8, CXCL1 and MCP1 are chemoattractant proteins. As these chemoattractants are released at a high level when MSCs and cancer cells are in proximity they have a significant effect in MSC homing towards tumor cells (Id.).

To study the homing capability of MSCs into a tumor site in vivo, genetically modified GFP-expressing MDA-MB231 cells were injected intra-mammary into 4-6 weeks old NIHIII immune-deficient female mice (n=5). $5 \times 10^5$ MSCs were injected into the tail vein of these animals. The tumor tissues were extracted seven days following MSCs injections, and the tumor tissue was harvested, fixed, and subjected to immunohistochemistry using HNA antibody to detect the human cells and DAPI for staining DNA.

FIG. 1 shows the homing of MSCs in tumor site. These experiments confirm that MSCs are highly suitable to be used as delivery agents to deliver silencers to the tumor site as they preferably engraft to the tumor because they are attracted by respective cytokines produced and released by the tumor cells.

MSC Effect on Tumors

MSCs contribute to tumor growth in a number of ways, including their roles in expressing growth factors and enhancing vessel formation. Data has shown that the tumor microenvironment modifies MSCs' properties toward promoting breast cancer and metastasis, especially for MSCs residing in breast adipose tissue, called adipose derived stem cells or "ASCs".

To study the effect of insoluble factors on stromal cells, including MSCs, exosomes were purified from cultures of MDA-MB231 cells. MSCs were incubated with purified exosomes from MDA-MB231 cells ($MDA_{Exo}$) for 14 hours in 37° C. and 5% $CO_2$. The changes in the gene expression in MSCs were assessed, and the graphs illustrated in FIG. 2A-2D shows the genes modified following MSCs exposure to $MDA_{Exo}$.

Figure 3A:
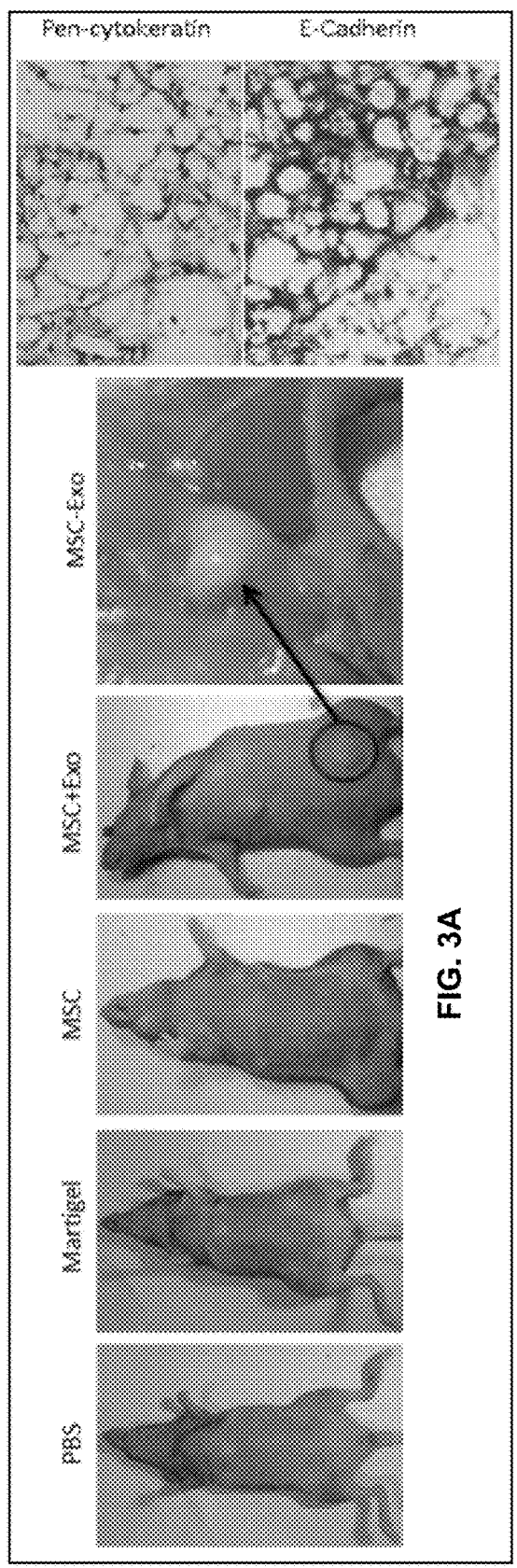
FIG. 3A shows intra-mammary engraftment of MSCs. The MSCs were exposed to purified $MDA_{Exo}$ for 14 hours and then $5 \times 10^5$ cells (in Martigel) were engrafted into mammary glands of NIHIII nude mice (female, 6-8 weeks old). The animals were observed for tumor growth weekly and euthanized after 12 weeks. Panels (from left to right) show the animals injected with PBS, Martigel, and unexposed MSCs as controls. The MSC-exposed animals develop tumors at the site of injection versus no visible tumors growing on the controls. The euthanized animals were dissected at week 12 post-engraftment. Histology on the tumor tissue show positive immuno-reaction to pencytokeratin E-cadherin antibodies (Lieca, 20×).
Figure 3C:
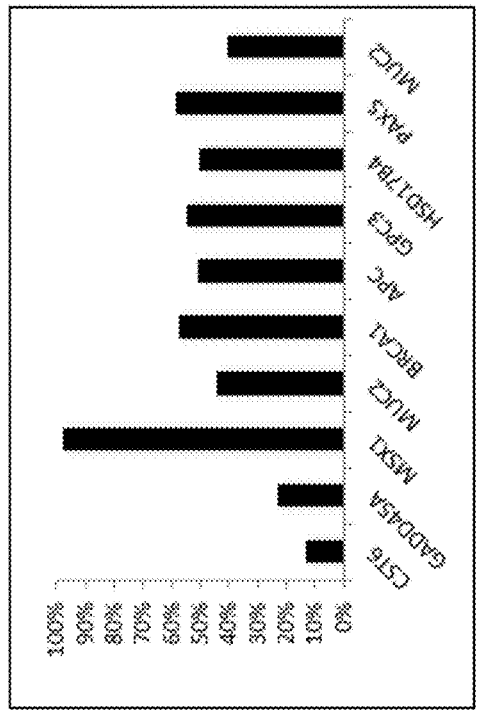
FIG. 3C shows methylated genes in MSCs. Using PCR array, the methylated genes were identified in MSCs exposed to MDA-MB-231 culture condition media and $MDA_{Exo}$ (n=3, p<0.05).
Figure 3B:
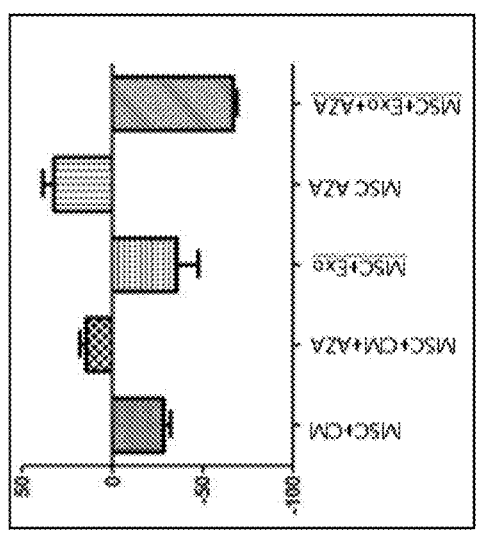
FIG. 3B shows methylation levels increased in exposed MSCs. MSCs exposed to MDA-MB-231 culture condition media and $MDA_{Exo}$ show enhanced levels of methylation; the methylation levels are reversible when exposed MSCs are treated with 5-Aza-2'-deoxycytidine (n=5, P<0.05).

The exosome exposed MSCs ($5 \times 10^5$) are called $MDA_{Exo}$ herein and were injected intra-mammary into NIHIII immune-deficient mice. The animals developed a growing tumor-like mass at the site of injection within 12 weeks, as shown in FIG. 3A. Exposure to either MDA-MB231 culture condition media or to $MDA_{Exo}$ enhances the methylation in MSCs, as seen in FIG. 3B. The methylation level was reversible when $MDA_{Exo}$-exposed MSCs were treated with 5-Aza-2'-deoxycytidine. The gene expression analysis showed several genes, including BRCA1, PAX5, and APC, were highly methylated, as shown by FIG. 3C.

Silencing TRAF3IP2 and/or RAB27A

Tumor microenvironment components that are initially released from breast cancer cells activate the key transcription factors in inflammatory and stromal cells, similar to those described in breast cancer cells. This leads to the production and release of inflammatory mediators, which proceed to trigger cancer-related inflammation. The IKK/NF-κB signaling pathway has been shown to transcriptionally regulate inflammatory cytokine expression, and both IKK and NF-κB have been targeted to reduce cancer-related inflammation in the tumor microenvironment. However, these approaches were unsuccessful due to the activation of alternative pathways such as Toll-like receptors (TLRs).

TRAF3IP2 encodes ACT1, a signaling adaptor involved in the regulation of adaptive immunity. Studies of TRAF3IP2-deficient mice suggest that TRAF3IP2 is a negative regulator of humoral immunity through its inhibitory effect on CD40- and BAFFR-mediated signaling. TRAF3IP2 operates as a positive signaling adaptor in IL-17-mediated cellular immune responses. IL-17 is a dominant 'signature' cytokine of TH-17 cells and up-regulates neutrophil-mobilizing cytokines, chemokines, and tissue-degrading matrix metalloproteases.

IL-17-dependent receptor ligation induces TRAF3IP2 recruitment to the cytoplasmic tail of the IL-17R. This in turn allows the incorporation of the TNF receptor-associated factors TRAF3 and TRAF6 into the signaling complex and the subsequent downstream activation of the MAPK and NF-κB pathway. Accordingly, TRAF3IP2 is not only involved in pathways balancing humoral and cellular immunity, but also represents a chief link between IL-17-mediated adaptive immune responses and NF-κB as the master regulator of innate immunity controlling the inducible transcription of various pro-inflammatory cytokines.

The data presented herein indicates that TRAF3IP2 mediates IKK dependent NF-κB activation as well as TLR4 signaling. It has been shown that IL-17 signals exclusively via TRAF3IP2, and TRAF3IP2 gene deletion abrogates IL-17-dependent inflammatory signaling. The novel findings of the present disclosure show a significantly high expression of TRAF3IP2 in breast cancer cells while this expression is minimal in non-malignant breast epithelial cells and MSCs.

Interestingly, the data presented here also show that the expression of RAB27A is also significantly higher in breast cancer cells compared to 184A1 cells, a non-malignant breast epithelial cell line, and MSCs, as shown in FIG. 4A. The silencing of RAB27A and TRAF3IP2 decrease the cell proliferation in MDA-MB231 cells, while the silencing of these genes has no effect on MSC replication capacity, as seen in FIG. 4B.

Silencing TRAF3IP2 in MDA-MB231 cells ($MDA_{KDTRAF3IP2}$) results in remarkable changes in expression of cytokines. Cytokine array analysis shows that the level of cytokines mostly involved in breast cancer progression and metastasis are significantly reduced in $MDA_{KDTRAF3IP2}$ cells, as shown in FIG. 4C.

Silencing TRAF3IP2 results in significant changes in the expression of factors involved in the formation of tumor microenvironment and associated inflammation. The tumor microenvironment is under constant chronic inflammatory pressure. It has been shown that one of the potent regulators of inflammation is TGF-β which was found to regulate the expression of angiopoietin-like 4 (ANGPTL4) via a Smad3-signaling pathway. The up-regulation of ANGPTL4 in cancer cells when they extravasate into the circulatory system likely explains their inclination toward colonizing lung tissue. The rationale for this is based on the ability of ANGPTL4 to disrupt the integrity of vascular tight junctions, thereby increasing the permeability of the capillaries in the lung to promote the intravasation into the lung tissue.

Figure 5:
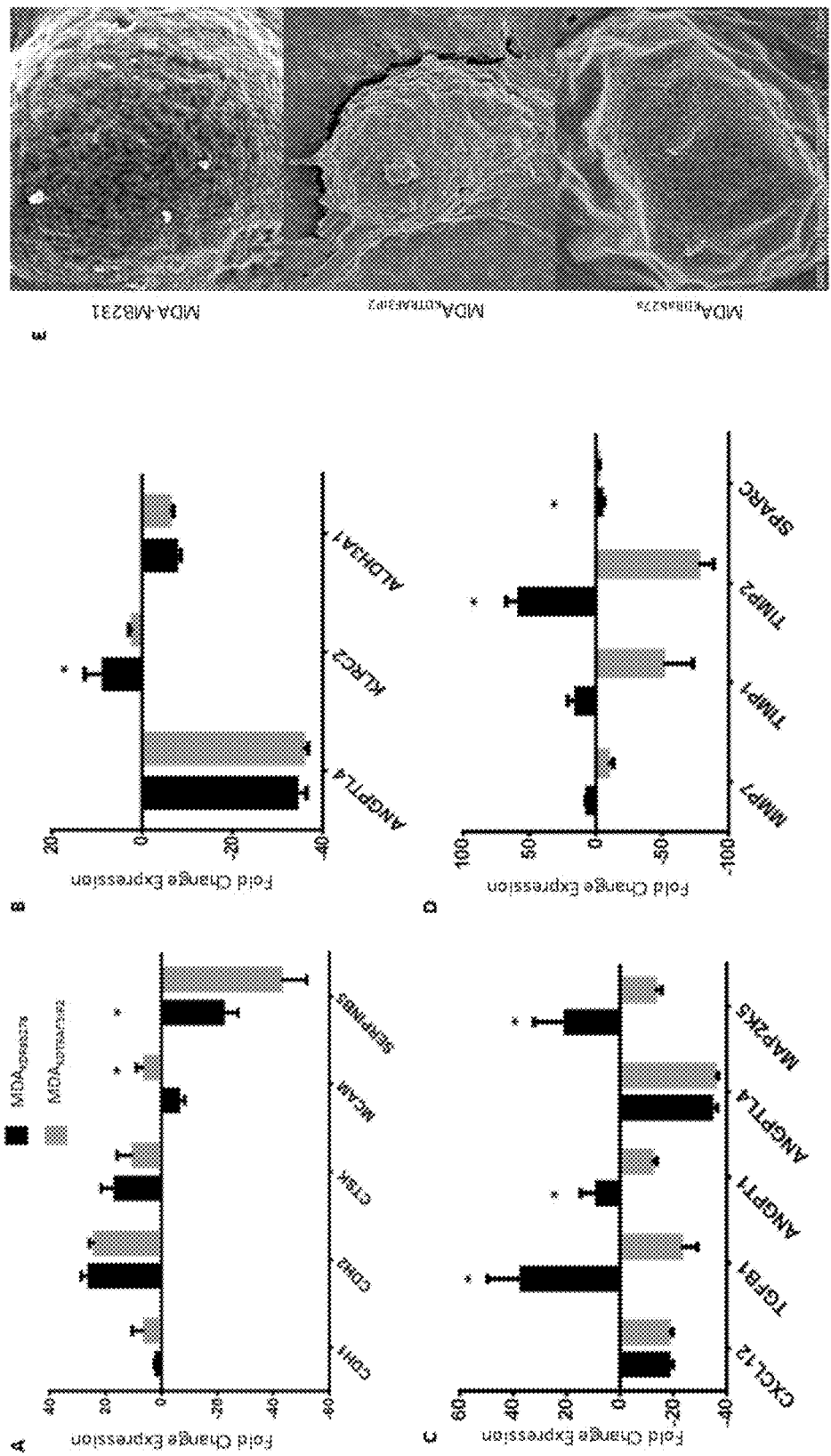
FIG. 5 shows the effect of silencing TRAF3IP2 and RAB27A on tumor cells. MDA-MB231 cells were silenced for the expression of TRAF3IP2 and RAB27A, then the selected gene expression was assessed using PCR array and compared to wild type cells set as zero in the graphs. The perturbed genes that displayed greater than two fold changed expression were grouped based on their function of cell adhesion (A), transcription factors (B), cell growth and proliferation (C), and extracellular matrix proteins (D). The graphs are representatives of triplicate experiments (P<0.05, * P<0.001). Panel (E) shows an electron micrograph of MDA-MB231, $MDA_{KDTRAF3IP2}$, and $MDA_{KDRAB27A}$ cells. The cells were negatively stained using uranyl acetate and viewed by electron microscopy. Inside images are with higher magnification; the scale bar represents 200 nm.

The present data shows a significant reduction in ANGPTL4 expression in both $MDA_{KDRab27}$ and $MDA_{KDTRAF3IP2}$, as seen in FIG. 5B. The expression of ANGPT1, which binds to extracellular matrix from carcinoma cells, is exclusively decreased in $MDA_{KDTRAF3IP2}$, while its expression is enhanced in $MDA_{KDRab27}$ cells, as shown by FIG. 5A-5D. This is due to the halt in exocytosis in MDA$_{KDRab27}$ cells. Electron microscopy indicates abnormal morphology in both MDA$_{KDRab27}$ and MDA$_{KDTRAF3IP2}$ cells.

Silencing In Vivo

The data presented above strongly suggests that silencing TRAF3IP2 and RAB27A could have potent effects in vivo, and thus, the next step was to deliver silencers to tumor cell using cancer cells that already contained the silencers.

In these experiments, the expression of TRAF3IP2 and RAB27A were silenced in MDA-MB231 cells using lentiviral-based vectors encoding silencer RNA. Female 4-6 weeks old NIHIII mice were injected intra-mammary with 1×10$^5$ MDA$_{KDTRAF3IP2}$ cells in PBS and Martigel. Another group of animals were injected with 1×10$^5$ MDA$_{KDRAB27A}$ cells in PBS and Martigel. As controls, a group of animals were injected with just 1×10$^5$ MDA-MB231 cells in PBS and Martigel, another group was injected with Matrigel, and another group was injected with PBS.

Earlier work showed that breast cancer cells exhibit significantly high levels of RAB27A expression and ultimately have higher exocytosis activity, as shown in FIG. 4A. These in vivo studies showed a decreased tumor volume in MDA$_{KDRAB27A}$ up to 30 weeks post-injection. The control group injected with MDA-MB231 cells showed tumor growth within 8 weeks and the animals were euthanized, as seen in FIG. 6A. Animals injected with MDA$_{KDTRAF3IP2}$ cells survived up to 52 weeks with only limited tumor growth.

Compared to animals injected with MDA-MB231 cells, the survival studies also show a 30 and 52 weeks life span for animals injected with MDA$_{KDRab27}$ and MDA$_{KDTRAF3IP2}$ cells, respectively, as shown by FIG. 6B. These results demonstrate that reducing exocytosis in breast cancer cells attenuates the release of oncogenic molecules into the tumor microenvironment in both soluble and insoluble forms. Silencing TRAF3IP2 regresses tumor growth by reducing cytokine signaling.

Figure 7:
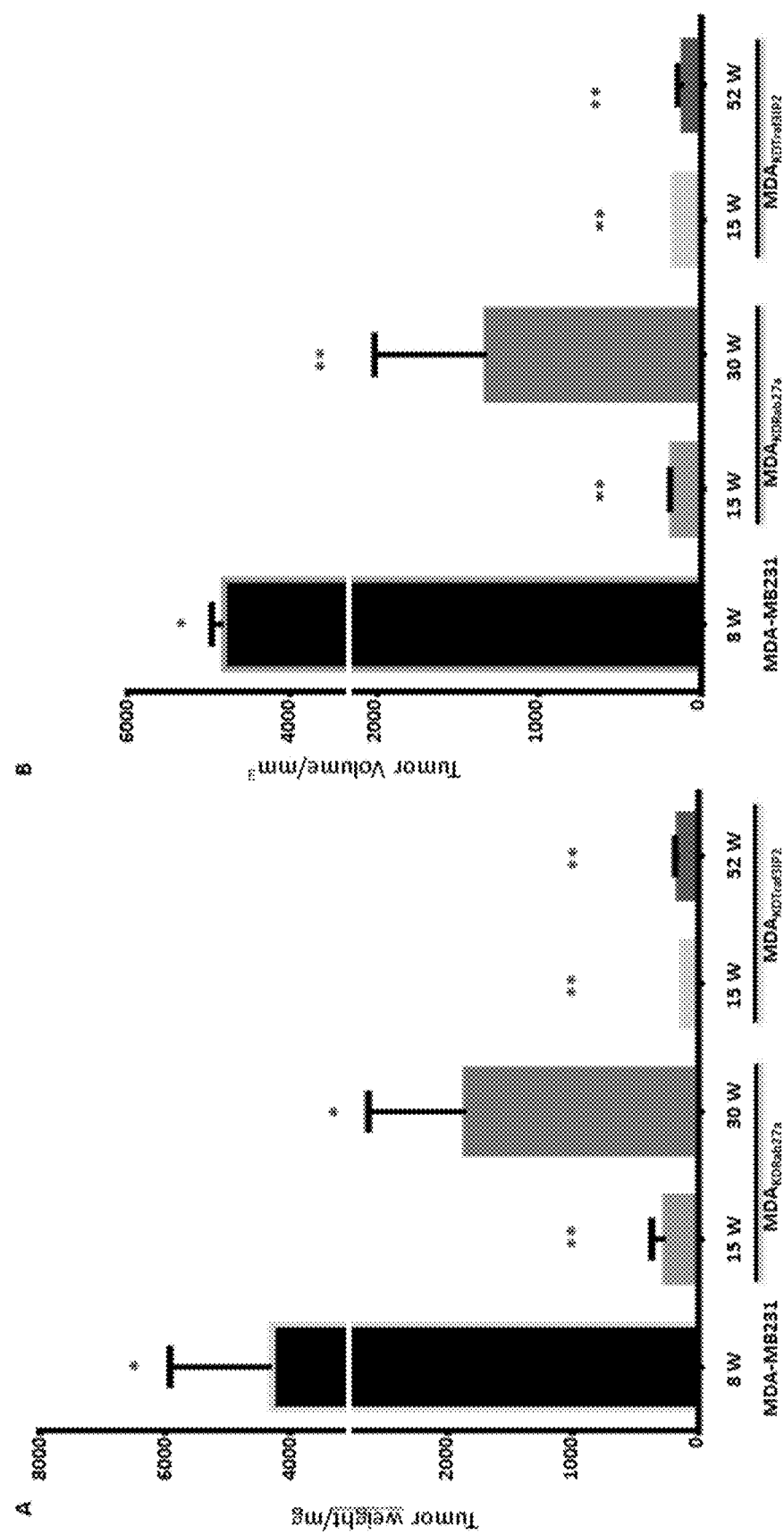
FIG. 7 shows graphs of xenograft tumor weight and volume. Animals injected with MDA-MB231, $MDA_{KDTRAF3IP2}$ and $MDA_{KDRAB27A}$ cells were sacrificed and tumors were isolated and weighted. A illustrates tumor weight and B displays tumor volume in injected animals at different time points.

Upon euthanizing the animals, the tumors were isolated and weighted to quantify the effects of the silencers. FIG. 7A shows the tumor weight and FIG. 7B shows the tumor size at 8 weeks post-injection of MDA-MB231 injected cells, at 30 weeks for MDA$_{KDTRAF3IP2}$ and MDA$_{KDRAB27A}$ cells, and at 52 weeks for MDA$_{KDTRAF3IP2}$ injected cells. These data indicate a significant decrease in tumor growth following down-regulation of TRAF3IP2 and RAB27A.

Thus, the data establishes that silencing TRAF3IP2 and RAB27A in tumor cells prevents tumor growth and/or metastasis in vivo. Injection of MDA-MB231 cells results in metastasis within 8 weeks (data not shown). However, postmortem analysis of animals injected with MDA$_{KDRab27}$ and MDA$_{KDTRAF3IP2}$ showed no metastasis at 30 weeks and 52 weeks post-injection (data not shown).

ΔTRAF3IP2

Delivery of gene silencers is one way of shutting down tRAF3IP2 and/or RAB27a, but knockouts are another possibility and also provide a good biological system in which to study the effects of silencing one or both of these genes.

Using the CRISPR/Cas system, the gene TRAF3IP2 and/or RAD27a can be knocked out. This strategy involves engineering specific nucleases (ex. CAS9-CRISPR) that are designed to create a DNA doublestrand break (DS-break) in the e.g., TRAF3IP2 gene, thereby activating the cell's endogenous homologous recombination repair pathway. Because the DS-break repair mechanisms are not accurate, changes are introduced into the gene by non-homologous end joining (NHEJ), which frequently lead to frame-shift mutations. In this system, CRISPR activation is under strict control of the IPTG promoter (an analog of lactose). Induction of this promoter activates the TRAF3IP2-specific CRISPR and causes mutations. The delivery of the TRAF3IP2-specific CRISPER lentiviral vectors will be attained by injection to the tumor site. Once the knock-outs are obtained, they can be used in studies to elucidate the biology of this system.

TRAF3IP2 Silencing

The above experiments were performed in an animal model, which mimicked breast cancer tumors. However, those tumors were not localized in the body, but scattered throughout, and especially subcutaneously. On this experiments, we show that the effect is reproducible in wild type mammary fat tumors.

Figure 9:
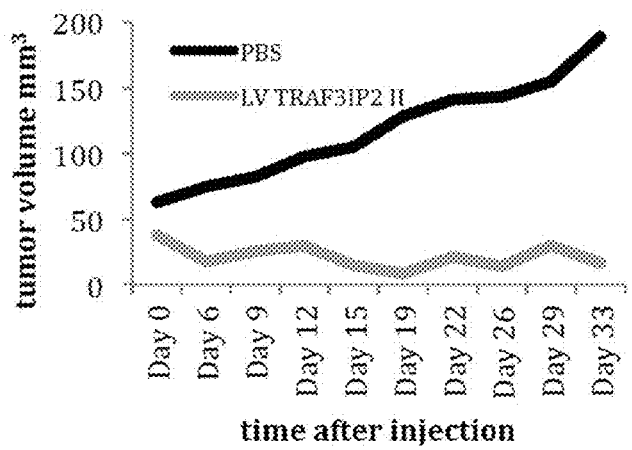
FIG. 9 shows tumor volume in treated animals with lentiviral vector carrying silencing sequence for TRAF3IP2 ($Lenti_{KDTRAF3IP2}$).

Tumors were generated in the mammary fat pad of female immune deficient NIHIII mice. For generating tumors, 5×10$^5$ MDA-MB-231 cells were mixed with 50 μl Matrigel and injected into the mammary fat pad. Ten days after injecting the MDA-MB-231 cells, NIH-III mice were randomly divided into two groups. One group of animals was received direct injections of 100 μl lentiviral-vector carrying TRAF3IP2 silencer RNA (in PBS) to the tumor site. The other group (control group), the animals received 100 μl of PBS. Injected tumor volumes were evaluated twice a week by measuring two orthogonal diameters with digital calipers. Tumor volume (V) was calculated using the following equation: $V=(a \times b^2)/2$, where "a" is the longer diameter and "b" the shorter diameter FIG. 9. As can be seen, there was little or no tumor growth in those tumors injected with silencer encoding expression vectors. Although the data is not yet available for RAB27A, we predict the results will be similar.

TRAF3IP2 Silencing in Glioblastoma

The above experiments were performed using breast cancer cell lines, but we also hoped that the method might be applicable to other solid tumors, and thus tested a glioblastoma derived cell line to confirm.

TRAF3IP2 exhibit significant role in the onset of tumor microenvironment and metastasis in solid tumors including Glioblastoma. TRAF3IP2, a signaling adaptor involved in the regulation of adaptive immunity operates as a positive signaling adaptor in IL-17-mediated cellular immune responses. IL-17 is a dominant 'signature' cytokine of TH-17 cells and up regulates neutrophil-mobilizing cytokines, chemokines, and tissue-degrading matrix metalloproteases17. IL-17-dependent receptor ligation induces TRAF3IP2 recruitment to the cytoplasmic tail of the IL-17R. This in turn allows the incorporation of the TNF receptor associated factors (TRAF) TRAF3 and TRAF6 into the signaling complex and the subsequent downstream activation of the MAPK and NF-κB pathway. Accordingly, TRAF3IP2 is not only involved in pathways balancing humoral and cellular immunity, but it also represents a chief link between IL-17 mediated adaptive immune responses and NF-κB as the master regulator of innate immunity controlling the inducible transcription of various pro-inflammatory cytokines.

Previously, our group and others showed that TRAF3IP2 mediates IKK dependent NF-kB activation as well as TLR4 signaling. It has been shown that IL-17 signals exclusively via TRAF3IP2, and TRAF3IP2 gene deletion abrogates IL-17-dependent inflammatory signaling.

We have shown a significantly high expression of TRAF3IP2 in breast cancer cells while this expression is minimal in non-malignant breast epithelial cells and MSCs. Our data indicate that similar to breast cancer, significant amounts of TRAF3IP2 express in glioblastoma cells (data not shown). Herein, we have studied the effect of TRAF3IP2 silencing on in vitro and in vivo characteristics of a glioblastoma cell line (U87).

Figure 10:
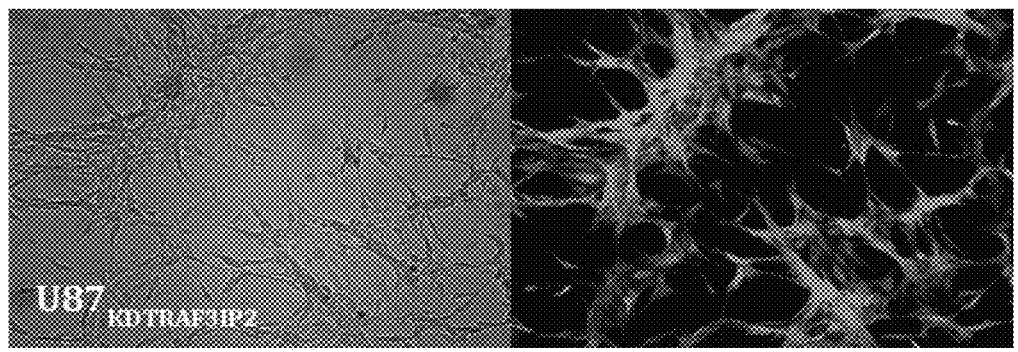
FIG. 10 is a photograph of U87 cells (a glioblastoma cell line) transduced with lentiviral vector carrying a silencing sequence for TRAF3IP2 and GFP (green).
Figure 11:
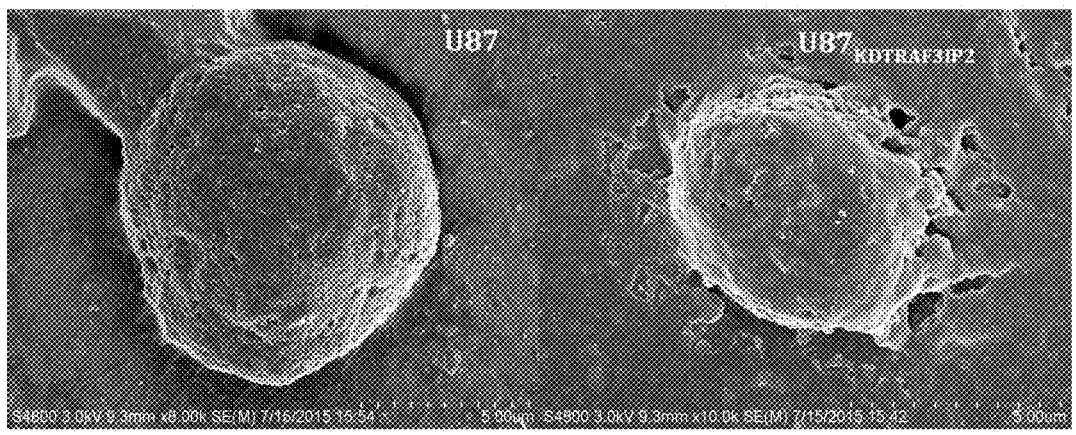
FIG. 11 shows a scanning electron micrograph showing morphological changes in U87$_{KDTRAF3IP2}$ compared to wild type U87.
Figure 12:
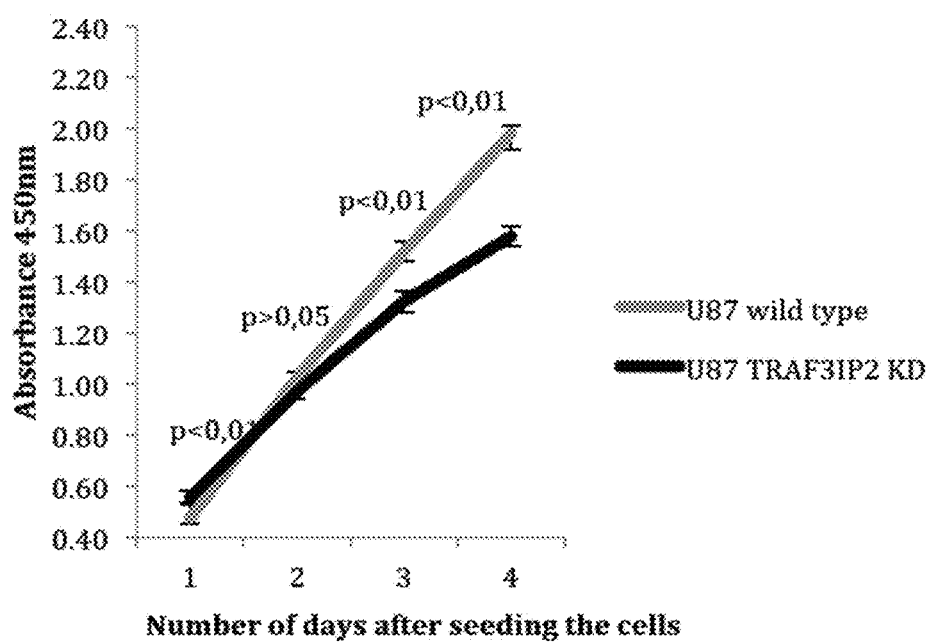
FIG. 12 is a cell proliferation assay showing a slight decrease in U87$_{KDTRAF3IP2}$ cell proliferation, as compared to the U87 wild type cell.

A human glioblastoma cell line "U87 cells" were transduced with lentiviral vector carrying a silencing sequence for TRAF3IP2 and GFP as a detectable marker. As can be seen in FIG. 10 transduced U87 cells with lentiviral delivering silencer sequences for TRAF3IP2. A GFP expressing sequence was used as a reporter gene making transduced cells traceable. In addition, electron microscopic analysis showed morphological changes in $U87_{KDTRAF3IP2}$ compared to wild type U87 (FIG. 11). These changes include a different cell morphology, which might be related to modified cellular function due to silencing TRAF3IP2.

A cell proliferation assay shown in FIG. 13 shows only a slight decrease in $U87_{KDTRAF3IP2}$ cell proliferation, as compared with the control cell U87, which suggests that the effect of the silencer is not a direct effect on cell proliferation, but an indirect one on the interaction of the tumor cells with its microenvironment.

Figure 14:
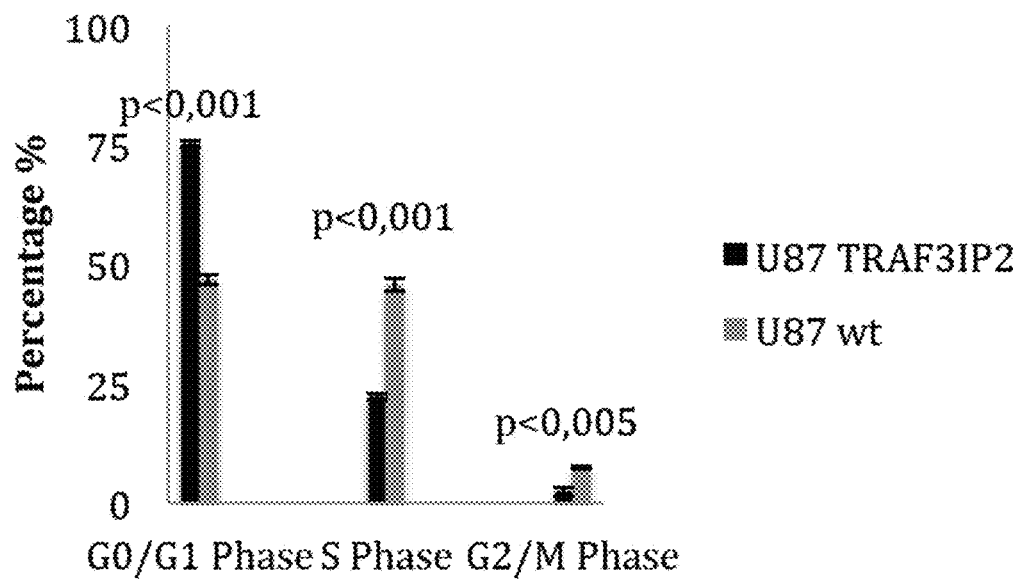
FIG. 14 is a cell cycle analysis of U87$_{KDTRAF3IP2}$ and wild type U87.

When we studied gene and protein expression levels, TRAF3IP2 expression was significantly reduced in both gene and protein levels in $U87_{KDTRAF3IP2}$ compared to control U87 and U87 transduced with scrambled silencer RNA (up to 92.3%), confirming that the silencer was effective in these cells. The results are shown in FIGS. 14A and 14B which provides the TRAF3IP2 gene and protein expression, respectively.

Figure 15:
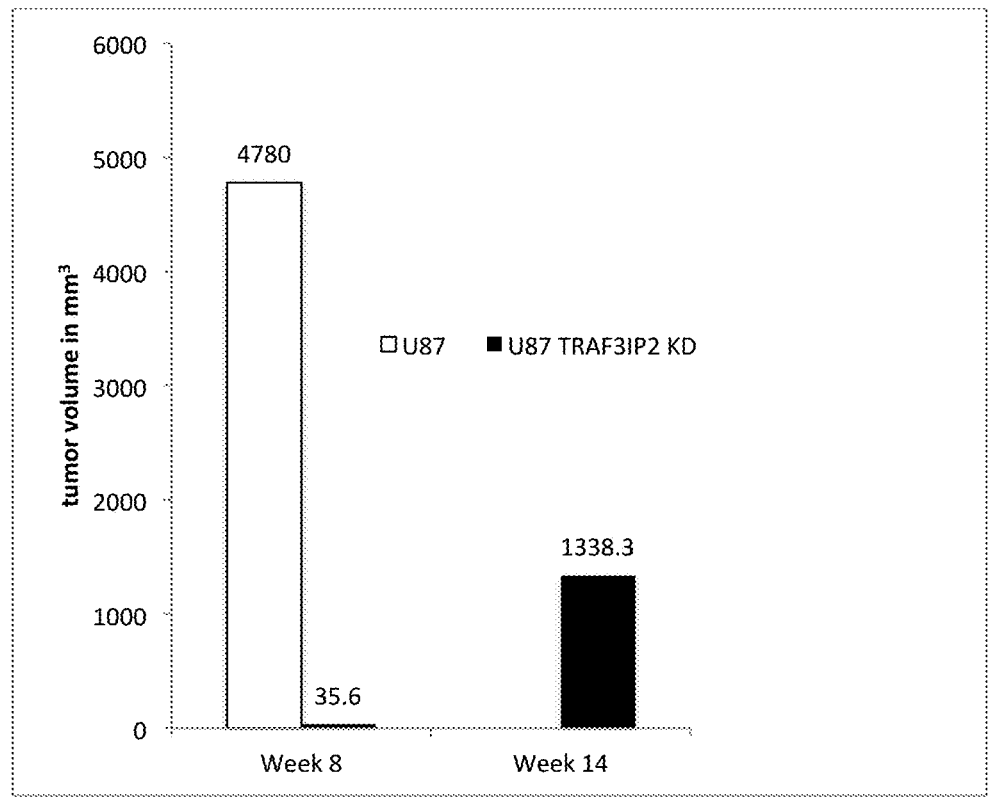
FIG. 15 shows the in vivo tumorigenesis of U87$_{KDTRAF3IP2}$ cells. Tumor size was measured using caliper and volume calculated and plotted here against time.

Cell cycle analysis also showed significant changes in cell cycle profile in $U87_{KDTRAF3IP2}$ compared to wild type U87. As seen in FIG. 15, silencing TRAF3IP2 caused higher G1 phase and lower populations in S and G2 phases, which might indicate a lower U87 replication rate.

In Vivo Tumorigenicity of U87KDTRAF3IP2

The above experiments strongly suggested that TRAF3IP2 silencer might also be effective in gliobalstoma tumors, but the results needed to be confirmed in an in vivo system. Therefore, we created U87 glioblastoma-like tumors by injecting these cells into nude mice.

$U87_{KDTRAF3IP2}$ and wild type U87 cells were injected subcutaneously in the upper portion of the right hind thigh. Tumors were measured with a traceable digital caliper (Fisher Scientific) for calculation of the tumor volume. The tumor size and volume were measured weekly. The animals injected with $U87_{KDTRAF3IP2}$ showed a significantly smaller tumor size compared to control animals injected with wild type U87. The control animals were sacrificed 8 weeks following injection. The animals injected with $U87_{KDTRAF3IP2}$ which were sacrificed on week 14 post-injection, showed significantly smaller tumor volume (FIG. 16). This confirms that TRAF3IP2 silencing can also slow gliobablastoma tumor growth in vivo.

Treatment of U87 tumors are also under investigation. Preliminary data shows a significant decrease in tumor development and growth on treated animals with lentiviral carrying silencer RNA injected to tumor site.

Future experiments include studies to confirm silencer delivery to mammary tumors, with preferred delivery agents such as MSCs. Of course, clinical studies will be performed eventually to confirm efficacy of these methods in humans, but these experiments are expected to take several years.

The following reference are incorporated by reference herein in its entirety for all purposes:

Hunter, C. A. (2007). "Act1-ivating IL-17 inflammation." Nat Immunol 8(3): 232-4.

Qian, Y., C. Liu, et al. (2007). "The adaptor Act1 is required for interleukin 17-dependent signaling associated with autoimmune and inflammatory disease." Nat Immunol 8(3): 247-56.

Senst, C., T. Nazari-Shafti, et al. (2013). "Prospective dual role of mesenchymal stem cells in breast tumor microenvironment." Breast Cancer Res Treat 137(1): 69-79.

WO2014030602 An agent for treating cancer

Xia Y F, et al., Identification of alternatively spliced Act1 and implications for its roles in oncogenesis, Biochem. Biophys. Res. Commun. 296 (2): 406-12 (2002).

What is claimed is:

1. A pharmaceutical composition for the treatment of a tumor having increased expression of TRAF3IP2, wherein said composition comprises at least one silencing sequence for TRAF3IP2 in a pharmaceutically acceptable nucleic acid carrier in an amount effective for the therapeutic treatment of a tumor, wherein said silencing sequence reduces the expression of the TRAF3IP2 gene by at least 65% as comparing to without the silencing sequence for TRAF3IP2, and wherein said silencing sequence is a modified portion of sense strand of SEQ ID NO. 7, wherein the portion is about 18-30 nt in length.

2. The composition of claim 1, wherein said composition comprises an expression vector encoding a TRAF3IP2 silencer operably coupled to an inducible promoter.

3. The composition of claim 1, wherein said composition further comprises an expression vector encoding a RAB27A silencer operably coupled to an inducible promoter.

4. The composition of claim 1, wherein said composition comprises at least one expression vector encoding a TRAF3IP2 silencer operably coupled to a first inducible promoter and additionally a RAB27A silencer operably coupled to a second inducible promoter in pharmaceutically acceptable nucleic acid carrier.

5. The composition of claim 4, wherein said first and second inducible promoter are activatable by the same ligand.

6. The composition of claim 1, wherein said silencer is an siRNA, an miRNA or an shRNA or an antisense RNA.

7. The composition of any of claim 1, said silencer encoded by an expression vector hosted in a mesenchymal stem cell (MSC) that targets said tumor.

8. The composition of claim 7, said MSC having been previously exposed to exosomes from said tumor.

9. The composition of claim 1, wherein said composition is formulated for parenteral administration, including direct injection into a tumor or its metastasis site by transcutaneous, intraarterial, intraductal, intravenous, intradermal, intramuscular, or subcutaneous administration.

10. A pharmaceutical composition for the treatment of a tumor having increased expression of TRAF3IP2, wherein said composition encodes at least one silencing sequence for TRAF3IP2 in a pharmaceutically acceptable nucleic acid carrier in an amount effective for the therapeutic treatment of a tumor, wherein said silencing sequence reduces the expression of a TRAF3IP2 gene by at least 65% as comparing to without the silencing sequence for TRAF3IP2, said silencing sequence comprising:

a) any one of SEQ ID NOs. 1-3 that is a modified portion of a sense strand of SEQ ID NO. 7;

b) about 18-30 nt RNA comprising a portion of sense strand of SEQ ID NO. 7 beginning with AA and ending with polyT, wherein the portion of sense strand of SEQ ID NO. 7 is a part of any of SEQ ID NOs. 1-3;

c) a modified portion of antisense RNA sequence from SEQ ID NO. 7, wherein the modified portion of antisense RNA sequence from SEQ ID NO. 7 is a part of any of SEQ ID NOs. 1-3;

d) an RNAse resistant 18-30 nt modified portion of antisense RNA sequence from SEQ ID NO. 7, wherein the modified portion of antisense RNA from SEQ ID NO. 7 is a part of any of SEQ ID NOs. 1-3; or e) about 18-30 nt RNA copy of a portion of SEQ ID NO. 7 having complementarity maintained in a first third of the RNA, but mismatches in a remainder of the RNA, wherein the complementary portion of SEQ ID NO. 7 is a part of any of SEQ ID NOs. 1-3.

11. The pharmaceutical composition of claim 1, wherein the silencing sequence is about 18-30 nt in length and is a part of any one of SEQ ID NOs. 1-3 that corresponds to the portion of sense strand of SEQ ID NO. 7.

12. The composition of claim 10, wherein said composition further comprises an expression vector encoding a RAB27A silencer operably coupled to an inducible promoter.

13. The composition of claim 10, wherein said composition is formulated for parenteral administration, including direct injection into a tumor or its metastasis site by transcutaneous, intraarterial, intraductal, intravenous, intradermal, intramuscular, or subcutaneous administration.

* * * * *